(12) United States Patent
Nothacker

(10) Patent No.: US 11,602,306 B2
(45) Date of Patent: Mar. 14, 2023

(54) METHOD AND SYSTEM FOR REMOTE TRANSDERMAL ALCOHOL MONITORING

(71) Applicant: KHN Solutions, Inc., San Francisco, CA (US)

(72) Inventor: Keith Harry Nothacker, San Francisco, CA (US)

(73) Assignee: KHN Solutions, Inc., San Francisco, CA (US)

( * ) Notice: Subject to any disclaimer, the term of this patent is extended or adjusted under 35 U.S.C. 154(b) by 0 days.

(21) Appl. No.: 17/574,278

(22) Filed: Jan. 12, 2022

(65) Prior Publication Data

US 2022/0218277 A1 Jul. 14, 2022

Related U.S. Application Data

(60) Provisional application No. 63/248,712, filed on Sep. 27, 2021, provisional application No. 63/136,598, filed on Jan. 12, 2021.

(51) Int. Cl.

| | | |
|---|---|---|
| *A61B 5/00* | (2006.01) | |
| *A61B 5/01* | (2006.01) | |
| *A61B 5/11* | (2006.01) | |
| *A61B 5/08* | (2006.01) | |

(52) U.S. Cl.
CPC .......... *A61B 5/4845* (2013.01); *A61B 5/0008* (2013.01); *A61B 5/01* (2013.01); *A61B 5/082* (2013.01); *A61B 5/11* (2013.01); *A61B 5/4809* (2013.01); *A61B 5/681* (2013.01); *A61B 5/7267* (2013.01); *A61B 5/7465* (2013.01)

(58) Field of Classification Search
CPC .. G08B 21/02; G08B 21/0453; A61B 5/0022; A61B 5/68–6829; A61B 5/6831
See application file for complete search history.

(56) References Cited

U.S. PATENT DOCUMENTS

| | | |
|---|---|---|
| 4,487,055 A | 12/1984 | Wolf |
| 4,738,333 A | 4/1988 | Collier et al. |
| 4,749,553 A | 6/1988 | Lopez et al. |

(Continued)

FOREIGN PATENT DOCUMENTS

| | | |
|---|---|---|
| FR | 2975522 A1 | 11/2012 |
| KR | 100673261 B1 | 1/2007 |

OTHER PUBLICATIONS

Kim, J et al. Noninvasive alcohol monitoring using a wearable tattoo-based iontophoretic-biosensing system. ACS Sensors. Jul. 12, 2016. vol. 1. No. 8; abstract.

(Continued)

*Primary Examiner* — Shirley X Jian
(74) *Attorney, Agent, or Firm* — Jeffrey Schox; Caitlin Ploch

(57) ABSTRACT

A system for remote transdermal alcohol monitoring includes and/or interfaces with a transdermal alcohol sensing device. Additionally or alternatively, the system can include and/or interface with any or all of: a user device; a supplementary alcohol sensing device; a set of supplementary sensors; a computing subsystem; a user interface; and/or any other components. A method for remote transdermal alcohol monitoring includes: receiving a set of inputs; determining a set of outputs; and triggering an action based on the set of outputs.

20 Claims, 18 Drawing Sheets
(9 of 18 Drawing Sheet(s) Filed in Color)

(56) References Cited

U.S. PATENT DOCUMENTS

| | | |
|---|---|---|
| 4,902,628 A | 2/1990 | Blair |
| 4,914,038 A | 4/1990 | Jewitt |
| 4,996,161 A | 2/1991 | Conners et al. |
| D333,441 S | 2/1993 | Greene |
| 5,216,415 A | 6/1993 | Ono et al. |
| 5,220,919 A | 6/1993 | Phillips et al. |
| 5,291,898 A | 3/1994 | Wolf |
| 5,416,468 A | 5/1995 | Baumann |
| 5,426,415 A | 6/1995 | Prachar et al. |
| 5,433,863 A | 7/1995 | Braden et al. |
| D362,642 S | 9/1995 | Howse |
| D381,885 S | 8/1997 | Lane |
| 5,944,661 A | 8/1999 | Swette et al. |
| 6,026,674 A | 2/2000 | Gammenthaler |
| 6,075,444 A | 6/2000 | Sohege et al. |
| 6,433,863 B1 | 8/2002 | Weiss |
| 6,454,723 B1 | 9/2002 | Montagnino |
| 6,556,905 B1 | 4/2003 | Mittelsteadt et al. |
| 6,608,399 B2 | 8/2003 | McConnell et al. |
| 6,726,636 B2 | 4/2004 | Der et al. |
| 6,748,792 B1 | 6/2004 | Freund et al. |
| 6,824,520 B2 | 11/2004 | Orr et al. |
| 6,853,956 B2 | 2/2005 | Ballard et al. |
| 6,858,182 B1 | 2/2005 | Ito et al. |
| 6,899,683 B2 | 5/2005 | Mault et al. |
| 6,956,484 B2 | 10/2005 | Crespo |
| 6,958,691 B1 | 10/2005 | Anderson et al. |
| D521,885 S | 5/2006 | Eddy et al. |
| D530,424 S | 10/2006 | Manser et al. |
| D539,683 S | 4/2007 | Shaw et al. |
| D539,684 S | 4/2007 | Kitamura et al. |
| 7,204,335 B2 | 4/2007 | Stewart et al. |
| 7,256,700 B1 | 8/2007 | Ruocco et al. |
| 7,311,665 B2 | 12/2007 | Hawthorne et al. |
| 7,341,693 B2 | 3/2008 | Der et al. |
| 7,451,852 B2 | 11/2008 | Stewart et al. |
| 7,462,149 B2 | 12/2008 | Hawthorne et al. |
| D586,677 S | 2/2009 | Nothacker et al. |
| D603,281 S | 11/2009 | Gonzalez |
| 7,611,461 B2 | 11/2009 | Hawthorne et al. |
| 7,611,611 B2 | 11/2009 | Belt |
| D606,434 S | 12/2009 | Castrodale et al. |
| 7,636,047 B1 | 12/2009 | Sempek |
| 7,641,611 B2 | 1/2010 | Hawthorne et al. |
| 7,823,681 B2 | 11/2010 | Crespo et al. |
| 7,930,927 B2 | 4/2011 | Cooper et al. |
| 7,934,577 B2 | 5/2011 | Walter et al. |
| 3,040,233 A1 | 10/2011 | Adappa et al. |
| 8,078,334 B2 | 12/2011 | Goodrich |
| 8,126,735 B2 | 2/2012 | Dicks et al. |
| 8,165,824 B2 | 4/2012 | Iiams et al. |
| 8,240,419 B2 | 8/2012 | Zimmermann et al. |
| 8,258,968 B2 | 9/2012 | Ghazarian et al. |
| 8,280,436 B2 | 10/2012 | Harris |
| 8,317,697 B2 | 11/2012 | Hawthorne et al. |
| 8,359,901 B2 | 1/2013 | Freund et al. |
| 8,370,027 B2 | 2/2013 | Pettersson et al. |
| 8,381,573 B2 | 2/2013 | Keays |
| 8,453,492 B2 | 6/2013 | Tsuzuki et al. |
| 8,466,796 B1 | 6/2013 | Mejia et al. |
| 8,505,360 B2 | 8/2013 | Ruocco et al. |
| 8,525,668 B1 | 9/2013 | Alouani et al. |
| 8,549,318 B2 | 10/2013 | White et al. |
| 8,590,364 B2 | 11/2013 | Lopez et al. |
| 8,657,744 B2 | 2/2014 | Rompa et al. |
| 8,693,597 B2 | 4/2014 | Sexton et al. |
| 8,707,758 B2 | 4/2014 | Keays |
| D705,100 S | 5/2014 | Nothacker et al. |
| 8,808,228 B2 | 8/2014 | Brister et al. |
| 8,814,804 B2 | 8/2014 | Walden et al. |
| 8,849,387 B2 | 9/2014 | Gilbert et al. |
| 8,862,152 B1* | 10/2014 | Buchholz ............... G08B 21/02 |
| | | 455/456.1 |
| 8,878,669 B2 | 11/2014 | Nothacker et al. |
| 8,920,725 B2 | 12/2014 | Withrow et al. |
| 8,941,501 B1 | 1/2015 | Debijl |
| 8,957,771 B2 | 2/2015 | Arringdale et al. |
| D724,980 S | 3/2015 | Nothacker et al. |
| D727,763 S | 4/2015 | Nothacker et al. |
| D727,764 S | 4/2015 | Nothacker et al. |
| 9,011,657 B2 | 4/2015 | Parselle et al. |
| 9,020,773 B2 | 4/2015 | Son et al. |
| D731,341 S | 6/2015 | Kobayakawa |
| 9,045,101 B2 | 6/2015 | Phelan |
| 9,063,120 B2 | 6/2015 | Park |
| 9,076,317 B2 | 7/2015 | Nothacker et al. |
| 9,095,251 B2 | 8/2015 | Purks et al. |
| 9,192,324 B2 | 11/2015 | Phillips et al. |
| 9,192,334 B2 | 11/2015 | Nothacker et al. |
| 9,228,997 B2 | 1/2016 | Keays |
| 9,239,323 B2 | 1/2016 | Keays |
| 9,241,659 B2 | 1/2016 | Rompa et al. |
| 9,241,661 B2 | 1/2016 | Shnaper et al. |
| 9,250,228 B2 | 2/2016 | Nothacker et al. |
| 9,278,696 B2 | 3/2016 | Yi et al. |
| 9,301,719 B2 | 4/2016 | Abreu |
| 9,398,858 B2 | 7/2016 | Phillips et al. |
| 9,417,232 B2 | 8/2016 | Keays et al. |
| 9,442,103 B1 | 9/2016 | Goad |
| 9,481,245 B2 | 11/2016 | Nelson |
| 9,489,487 B2 | 11/2016 | Hawthorne et al. |
| 9,662,065 B2 | 5/2017 | Nothacker et al. |
| 9,746,456 B2 | 8/2017 | Keays |
| 9,781,984 B2 | 10/2017 | Baranski et al. |
| 9,788,772 B2 | 10/2017 | Nothacker et al. |
| 9,820,114 B2 | 11/2017 | Greenhut et al. |
| 9,829,480 B2 | 11/2017 | Wojcik et al. |
| 9,848,815 B2 | 12/2017 | Abreu |
| 9,855,000 B2 | 1/2018 | Lansdorp et al. |
| 9,867,539 B2 | 1/2018 | Heikenfeld et al. |
| 9,872,649 B2 | 1/2018 | Nothacker et al. |
| 9,881,997 B2 | 1/2018 | Sakata et al. |
| 9,915,644 B2 | 3/2018 | Nothacker et al. |
| 9,922,508 B2 | 3/2018 | Keays et al. |
| 10,040,349 B2 | 8/2018 | Devries et al. |
| 10,182,752 B2 | 1/2019 | Nothacker et al. |
| 10,352,923 B2 | 7/2019 | Nothacker et al. |
| 10,631,767 B2 | 4/2020 | Nothacker et al. |
| 10,987,038 B2 | 4/2021 | Nothacker et al. |
| 11,324,449 B2* | 5/2022 | Nothacker ............ G01L 3/1435 |
| 2002/0008966 A1 | 1/2002 | Fjelstad et al. |
| 2002/0084130 A1 | 7/2002 | Der et al. |
| 2002/0089660 A1 | 7/2002 | Weiss |
| 2002/0128769 A1 | 9/2002 | Der et al. |
| 2002/0140289 A1 | 10/2002 | McConnell et al. |
| 2002/0143267 A1 | 10/2002 | Montagnino |
| 2003/0028120 A1 | 2/2003 | Mault et al. |
| 2003/0116159 A1 | 6/2003 | Orr et al. |
| 2003/0117287 A1 | 6/2003 | Crespo |
| 2003/0176803 A1 | 9/2003 | Gollar |
| 2003/0177119 A1 | 9/2003 | Cole |
| 2004/0236199 A1 | 11/2004 | Hawthorne et al. |
| 2004/0242976 A1 | 12/2004 | Abreu |
| 2005/0184870 A1* | 8/2005 | Galperin ............ G08B 13/2462 |
| | | 340/568.2 |
| 2005/0241871 A1 | 11/2005 | Stewart et al. |
| 2006/0182661 A1 | 8/2006 | Aquila |
| 2006/0193749 A1 | 8/2006 | Ghazarian et al. |
| 2006/0217624 A1 | 9/2006 | Myklebust et al. |
| 2006/0217625 A1 | 9/2006 | Forrester |
| 2006/0237252 A1* | 10/2006 | Mobley ................ B60K 28/063 |
| | | 340/576 |
| 2006/0237253 A1 | 10/2006 | Mobley et al. |
| 2006/0282344 A1 | 12/2006 | Brown |
| 2006/0293613 A1 | 12/2006 | Fatehi et al. |
| 2007/0024454 A1 | 2/2007 | Singhal |
| 2007/0093725 A1 | 4/2007 | Shaw |
| 2007/0144812 A1 | 6/2007 | Stewart et al. |
| 2007/0296601 A1 | 12/2007 | Sultan et al. |
| 2008/0045806 A1 | 2/2008 | Keppler |
| 2008/0097793 A1 | 4/2008 | Dicks et al. |
| 2008/0169924 A1 | 7/2008 | Belden |
| 2008/0183388 A1 | 7/2008 | Goodrich |

(56) References Cited

U.S. PATENT DOCUMENTS

| | | | |
|---|---|---|---|
| 2008/0216561 A1* | 9/2008 | Cooper | A61B 5/681 |
| | | | 73/53.01 |
| 2008/0262469 A1 | 10/2008 | Brister et al. | |
| 2009/0043409 A1 | 2/2009 | Ota | |
| 2009/0090577 A1 | 4/2009 | Takahashi et al. | |
| 2009/0182216 A1 | 7/2009 | Roushey et al. | |
| 2009/0201138 A1 | 8/2009 | Ghazarian et al. | |
| 2009/0212957 A1* | 8/2009 | Burris | G08B 23/00 |
| | | | 340/573.4 |
| 2009/0309711 A1 | 12/2009 | Adappa et al. | |
| 2010/0010689 A1 | 1/2010 | Yasushi et al. | |
| 2010/0012417 A1 | 1/2010 | Walter et al. | |
| 2010/0108425 A1 | 5/2010 | Crespo et al. | |
| 2010/0152976 A1 | 6/2010 | White et al. | |
| 2010/0234064 A1 | 9/2010 | Harris | |
| 2010/0268425 A1 | 10/2010 | Pei et al. | |
| 2010/0274411 A1 | 10/2010 | Ozaki | |
| 2010/0310011 A1 | 12/2010 | Sexton et al. | |
| 2011/0079073 A1 | 4/2011 | Keays | |
| 2011/0304465 A1 | 12/2011 | Boult et al. | |
| 2011/0308297 A1 | 12/2011 | Tsuzuki et al. | |
| 2011/0309932 A1 | 12/2011 | Arringdale et al. | |
| 2012/0020837 A1 | 1/2012 | Withrow et al. | |
| 2012/0075094 A1 | 3/2012 | Keays | |
| 2012/0132524 A1 | 5/2012 | Parselle et al. | |
| 2012/0157871 A1 | 6/2012 | Walden et al. | |
| 2012/0330175 A1 | 12/2012 | Phillips et al. | |
| 2013/0021153 A1 | 1/2013 | Keays | |
| 2013/0035602 A1 | 2/2013 | Gemer | |
| 2013/0111979 A1 | 5/2013 | Park | |
| 2013/0123570 A1 | 5/2013 | Ly et al. | |
| 2013/0150727 A1 | 6/2013 | Phillips et al. | |
| 2013/0218039 A1 | 8/2013 | Sotos et al. | |
| 2013/0253360 A1 | 9/2013 | Wang et al. | |
| 2013/0282321 A1 | 10/2013 | Son et al. | |
| 2013/0305808 A1 | 11/2013 | Yoo | |
| 2014/0012143 A1 | 1/2014 | Gilbert et al. | |
| 2014/0032596 A1 | 1/2014 | Fish et al. | |
| 2014/0052567 A1 | 2/2014 | Bhardwaj et al. | |
| 2014/0059066 A1* | 2/2014 | Koloskov | G16Z 99/00 |
| | | | 361/679.01 |
| 2014/0062703 A1 | 3/2014 | Purks et al. | |
| 2014/0062722 A1 | 3/2014 | Ofir et al. | |
| 2014/0086590 A1 | 3/2014 | Ganick et al. | |
| 2014/0165697 A1 | 6/2014 | Mochizuki et al. | |
| 2014/0165698 A1 | 6/2014 | Mochizuki et al. | |
| 2014/0188398 A1* | 7/2014 | Cohen | A61B 5/14532 |
| | | | 702/19 |
| 2014/0204334 A1 | 7/2014 | Stoll | |
| 2014/0210627 A1 | 7/2014 | Nothacker et al. | |
| 2014/0234172 A1 | 8/2014 | Burgi et al. | |
| 2014/0240132 A1 | 8/2014 | Bychkov | |
| 2014/0273858 A1 | 9/2014 | Panther et al. | |
| 2014/0281523 A1 | 9/2014 | Golino | |
| 2014/0303836 A1 | 10/2014 | Phelan | |
| 2014/0311215 A1 | 10/2014 | Keays et al. | |
| 2014/0361900 A1 | 12/2014 | Nothacker et al. | |
| 2014/0365142 A1 | 12/2014 | Baldwin | |
| 2014/0371603 A1 | 12/2014 | Fujita et al. | |
| 2015/0084774 A1 | 3/2015 | Wojcik et al. | |
| 2015/0164416 A1 | 6/2015 | Nothacker et al. | |
| 2015/0251660 A1 | 9/2015 | Nelson | |
| 2015/0325104 A1 | 11/2015 | Greenhut et al. | |
| 2015/0359469 A1 | 12/2015 | Jacobs et al. | |
| 2015/0360696 A1 | 12/2015 | Yi et al. | |
| 2016/0021228 A1 | 1/2016 | Roberts | |
| 2016/0284200 A1 | 9/2016 | Song et al. | |
| 2016/0324442 A1 | 11/2016 | Zdeblick | |
| 2016/0338627 A1 | 11/2016 | Lansdorp et al. | |
| 2017/0079574 A1 | 3/2017 | Rodriguez Restrepo et al. | |
| 2017/0086714 A1 | 3/2017 | Nothacker et al. | |
| 2017/0086743 A1 | 3/2017 | Bushnell et al. | |
| 2017/0103166 A1 | 4/2017 | Oh et al. | |
| 2017/0231571 A1 | 8/2017 | Rogers et al. | |
| 2017/0303819 A1 | 10/2017 | Nothacker et al. | |
| 2017/0313189 A1 | 11/2017 | Walter et al. | |
| 2017/0354354 A1 | 12/2017 | Nothacker et al. | |
| 2018/0085058 A1 | 3/2018 | Chakravarthi et al. | |
| 2018/0086264 A1 | 3/2018 | Pedersen | |
| 2018/0164285 A1 | 6/2018 | Nothacker et al. | |
| 2018/0184920 A1 | 7/2018 | Rabinovich et al. | |
| 2018/0209955 A1* | 7/2018 | Moeller | A61B 5/1477 |
| 2018/0263538 A1 | 9/2018 | Heikenfeld et al. | |
| 2019/0246958 A1 | 8/2019 | Moeller et al. | |
| 2019/0290197 A1* | 9/2019 | Nothacker | A61B 5/4845 |
| 2020/0101982 A1 | 4/2020 | Bowers et al. | |
| 2022/0192597 A1* | 6/2022 | Feldman | A61B 5/4845 |

OTHER PUBLICATIONS

Kuswandi, B et al. A simple visual ethanol biosensor based on alcohol oxidase immobilized onto polyaniline film for halal verification of fermented beverage samples. Sensors. 2014. vol. 14. No. 2; p. 2144, figure 6.

STIC Search Results. 15205876-528781-Search Results.pdf.

Zettl, Robert J., "The Determination of Blood Alcohol Concentration by Transdermal Measurement", Commissioned by Alcohol Monitoring Systems, Inc., Highlands Ranch, Colorado, Jul. 2002, 13 pages.

* cited by examiner video feed of monitored user showing monitored user's face and transdermal alcohol sensing device Client application at user device User interface of remote monitoring entity User interface of remote monitoring entity User interface of remote monitoring entity

METHOD AND SYSTEM FOR REMOTE TRANSDERMAL ALCOHOL MONITORING

CROSS-REFERENCE TO RELATED APPLICATIONS

This application claims the benefit of U.S. Provisional Application No. 63/136,598, filed 12 Jan. 2021, and U.S. Provisional Application No. 63/248,712, filed 27 Sep. 2021, each of which is incorporated in its entirety by this reference.

TECHNICAL FIELD

This invention relates generally to the intoxication monitoring field, and more specifically to a new and useful system and method for remote transdermal alcohol monitoring in the intoxication monitoring field.

BACKGROUND

Alcohol use remains the third leading cause of death both in the United States (85,000 deaths annually) and worldwide (up to 2.5 million deaths annually). The economic costs associated with excessive drinking exceed $223 billion annually in the United States alone. Some of the objective methods for measuring alcohol, such as breathalyzers and biological assays, can have significant drawbacks, such as invasiveness, constant user interaction, and/or the inability to provide real-time (or near real-time) quantitative measurements of alcohol usage. Transdermal alcohol detection, which measures alcohol permeating through the skin and correlates that measurement with the blood alcohol concentration, has offered the capacity to provide a noninvasive, continuous, and quantitative measurement of bodily alcohol. The implementation of comfortable, discreet, reliable, and robust transdermal alcohol detection in the remote monitoring space, however, has yet to be done.

Thus, there is a need in the intoxication monitoring field to create an improved system and method for remote transdermal alcohol monitoring.

BRIEF DESCRIPTION OF THE FIGURES

The patent or application file contains at least one drawing executed in color. Copies of this patent or patent application publication with color drawing(s) will be provided by the Office upon request and payment of the necessary fee.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
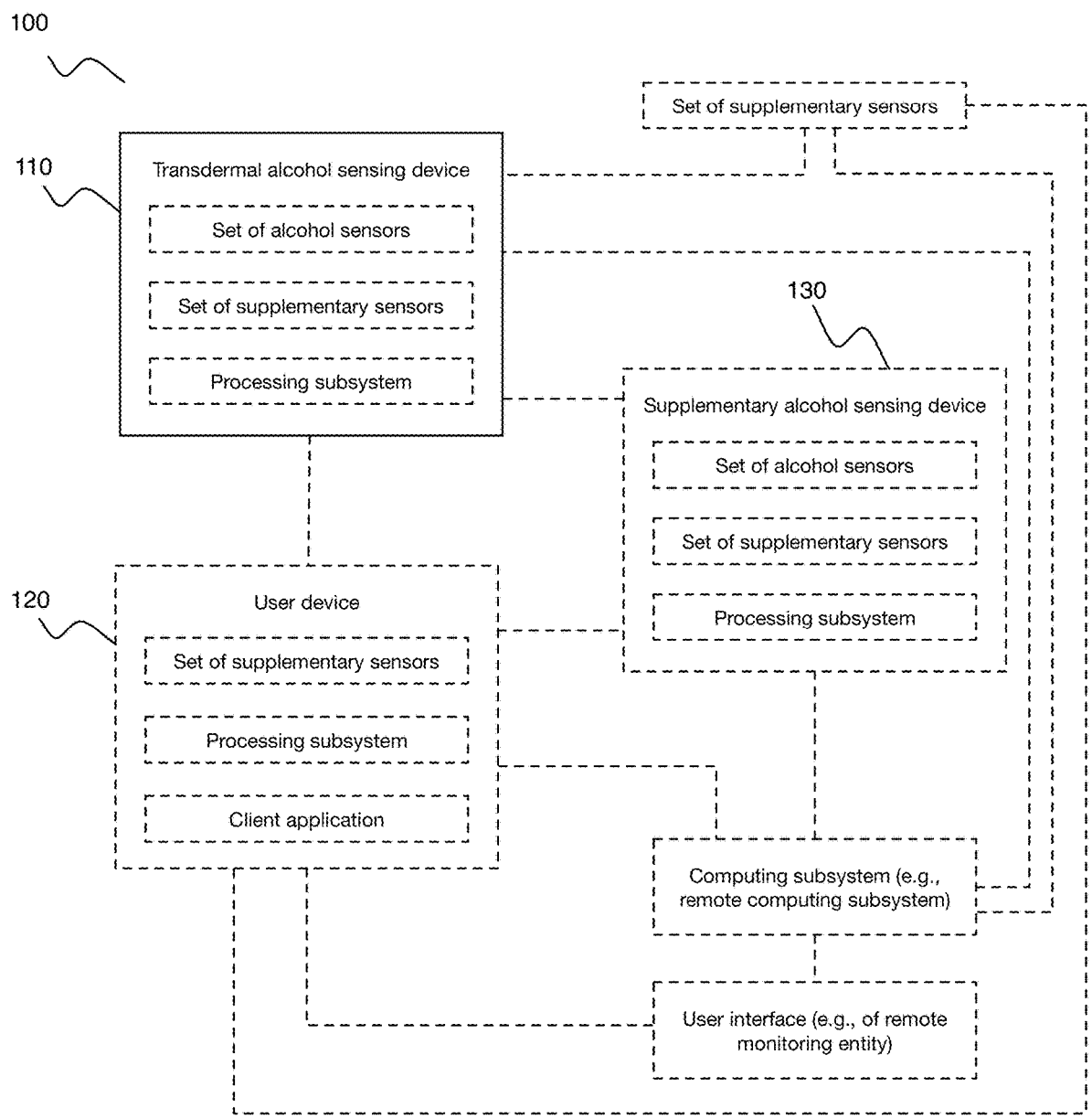
FIG. 1 is a schematic of a system for remote transdermal alcohol monitoring.

As shown in FIG. 1, a system 100 for remote transdermal alcohol monitoring includes and/or interfaces with a transdermal alcohol sensing device 110. Additionally or alternatively, the system 100 can include and/or interface with any or all of: a user device 120; a supplementary alcohol sensing device 130; a set of supplementary sensors; a computing subsystem; a user interface; and/or any other components. Further additionally or alternatively, the system 100 can include and/or interface with any or all of the components, systems, embodiments, and/or examples as described in any or all of: U.S. application Ser. No. 14/169,029, filed 30 Jan. 2014; U.S. application Ser. No. 14/602,919, filed 22 Jan. 2015; U.S. application Ser. No. 15/375,801, filed 12 Dec. 2016; U.S. application Ser. No. 16/362,444, filed 22 Mar. 2019; and U.S. application Ser. No. 17/033,501, filed 25 Sep. 2020, each of which is incorporated herein in its entirety by this reference.

Figure 2:
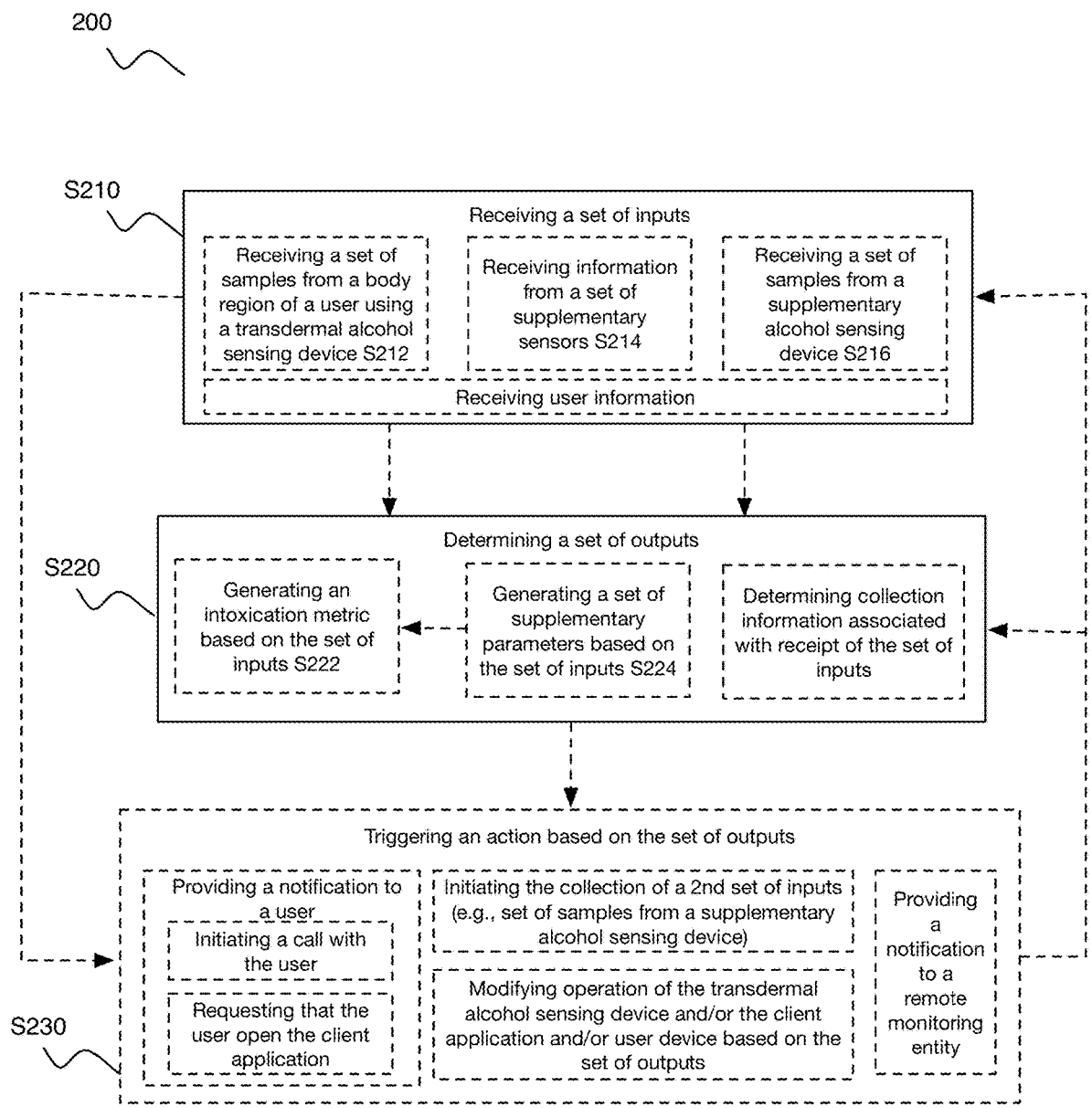
FIG. 2 is a schematic of a method for remote transdermal alcohol monitoring.

As shown in FIG. 2, a method 200 for remote transdermal alcohol monitoring includes: receiving a set of inputs S210; determining a set of outputs S220; and triggering an action based on the set of outputs S230. Additionally or alternatively, the method 200 can include and/or interface with any or all of the processes, methods, embodiments, and/or examples as described in any or all of: U.S. application Ser. No. 14/169,029, filed 30 Jan. 2014; U.S. application Ser. No. 14/602,919, filed 22 Jan. 2015; U.S. application Ser. No. 15/375,801, filed 12 Dec. 2016; U.S. application Ser. No. 16/362,444, filed 22 Mar. 2019; and U.S. application Ser. No. 17/033,501, filed 25 Sep. 2020, each of which is incorporated herein in its entirety by this reference, or any other suitable processes performed in any suitable order.

The method 200 is preferably performed with a system 100 as described above, but can additionally or alternatively be performed with any other suitable system.

2. Benefits

The system and method for remote transdermal alcohol monitoring can confer several benefits over current systems and methods.

In a first variation, the system and/or method confers the benefit of enabling remote monitoring of users for criminal justice and/or probation use cases through transdermal alcohol detection. In specific examples, the system confers the benefit of providing a tamper-proof, robust wearable transdermal alcohol sensing device and monitoring platform which can be used to collect intoxication information associated with the user, while the method implemented in conjunction with the system confers the benefit of reliably assessing data from the user. In specific examples, the method is configured to operate optimally even when the data is not received in a uniform fashion from the transdermal alcohol sensing device and/or other devices (e.g., user device) in communication with the transdermal alcohol sensing device.

In a specific example of the first variation, tampering and/or other deceptive intent of a user can be detected without requiring a specialized device or hardware component, but rather through the processing of sensor data associated with the device and/or user. Additionally or alternatively, tampering and/or other deceptive intent can be detected with a specialized device and/or hardware component (e.g., specialized fastener), a combination of a specialized device and sensor data processing, and/or through any other features or information.

In a second specific example of the first variation, a particular type of tampering can be determined and distinguished from others. This can include, for instance, but is not limited to, any or all of: removal of the device, obstruction of one or more sensors of the device, placement of the device on a different user, and/or any other forms of tampering.

In a second variation, additional or alternative to the first, the system and/or method confers the benefit of enabling secure and reliable remote monitoring of users for criminal justice and/or probation applications through transdermal alcohol detection with a transdermal alcohol sensing device and by way of a personal user device (e.g., smartphone) of the user. This can distribute the processing required for analyzing alcohol data and/or supplementary data among multiple devices and/or from the transdermal alcohol sensing device to the user device. This can, in turn, enable the transdermal alcohol sensing device to be portable, wearable, discreet, and/or otherwise less cumbersome than a device which does all the processing onboard.

In a third variation, additional or alternative to those described above, the system and/or method confers the benefit of enabling sensor data (e.g., indicating intoxication, indicating tampering, etc.) to be collected at a high frequency (e.g., at least once per minute, between 2-10 times per minute, etc.), such that remote monitoring entities (e.g., probation officers) can respond quickly in an event that alcohol and/or potential tampering have been detected, such that the remote monitoring entity can confirm (e.g., before the user has had time to become sober, before the user can continue to tamper with the device, etc.) and/or respond to the detection. This can enable a remote monitoring entity (e.g., a probation officer), for instance, upon detecting that a user is beginning to show signs of intoxication and/or tampering with the transdermal device, to quickly respond through any or all of: requiring the user to take a breathalyzer test, requiring the user to provide video of him or her (e.g., showing that he or she is wearing the transdermal device, showing that the transdermal device has not been tampered with, etc.); driving to the user's location; prompting a call with the user; and/or any other actions. Additionally or alternatively, any or all of these actions can be triggered and/or performed automatically (e.g., through automatically triggered notifications and/or instructions). In a set of specific examples, an alcohol sensor (e.g., fuel cell sensor) onboard the transdermal device is continuously or nearly continuously (e.g., every 10 seconds, every 20 seconds, every 30 seconds, between every 10 seconds and every 30 seconds, less than every 30 seconds, every minute, every 5 minutes, any interval in-between, etc.) sampling ambient air with a microporous membrane, which can allow more measurements to be taken and more frequently (e.g., as compared to sensors which require pumps and/or sample on average every 30 minutes), thereby providing a more actionable and comprehensive history of a user's sobriety/intoxication. Additionally or alternatively, the device can sample at a dynamic frequency, at a user-specific frequency (e.g., based on a level of threat associated with a user, based on a level of monitoring associated with the user, based on whether the user is a criminal offender vs. a general consumer, etc.), and/or at any other frequencies and with any suitable alcohol sensors.

In a fourth variation, additional or alternative to those described above, the system and/or method confers the benefit of prescribing (and/or configuring) optimal placement of the transdermal device on any or all users with respect to: accurate alcohol sensing, minimization of false positives, minimization of false negatives, user comfort, discreet placement, and/or any other features. In a set of specific examples, the transdermal sensing device is configured to be worn at a wrist region of the user. This can function, for instance, to prevent a conventional limitation associated with transdermal sensing devices placed closer to the ground (e.g., at the ankle, on the leg, etc.), which is the occurrence of false positives due to alcohol and/or alcohol vapors falling to and/or collecting at the ground of establishments (e.g., bars, concerts, parties, etc.) associated with high volumes of alcohol. Additionally or alternatively, the placement of the transdermal sensing device (e.g., at the wrist, at another region, etc.) can be configured to collect the most accurate and/or robust data (e.g., to detect a drinking event earliest, to detect a drinking event most accurately, etc.) associated with a user's intoxication, such as through placement at a skin surface associated with relatively thin layer(s) of skin and/or large blood flow (e.g., large number of veins and/or arteries), such as an inner wrist region of the user (which equivalently refers herein to a side of the wrist proximal the palm of the user's hand), which the inventors have found is advantageous for detecting intoxication.

In a fifth variation, additional or alternative to those described above, the system and/or method confers the benefit of dynamically determining and/or adapting actions which are triggered for any or all of the users (e.g., in response to detecting intoxication of the user, in response to not receiving data from the user's device, etc.), thereby taking into account any or all of: one or more schedules associated with the user, historical information associated with the user, preferences associated with the user, preferences associated with a remote monitoring entity responsible for the user, a level of risk and/or severity associated with the user (e.g., known offender, criminal offender, high risk, etc.), and/or any other factors. In a set of specific examples, for instance, in an event that data is not being received from the user's user device (e.g., within a threshold period of time since the last data was received), if it is occurring at a time when the user is likely sleeping (e.g., and/or when background syncing frequencies are typically low and/or especially irregular, and/or if the user is low risk, etc.), the threshold time waited until the user is contacted (e.g., and requested to foreground the client application, and requested to take a breathalyzer test, etc.) can be extended. Additionally or alternatively, the type of action triggered (e.g., breathalyzer test vs. being visited by a probation officer) and/or any other actions can be altered depending on the user and/or other information (e.g., temporal parameters).

Additionally or alternatively, the system and method can confer any other benefit.

3. System

As shown in FIG. 1, a system 100 for remote transdermal alcohol monitoring includes and/or interfaces with a transdermal alcohol sensing device no. Additionally or alternatively, the system 100 can include and/or interface with any or all of: a user device 120; a supplementary alcohol sensing device 130; a set of supplementary sensors; a computing subsystem; a user interface; and/or any other components. Further additionally or alternatively, the system 100 can include and/or interface with any or all of the components, systems, embodiments, and/or examples as described in any or all of: U.S. application Ser. No. 14/169,029, filed 30 Jan. 2014; U.S. application Ser. No. 14/602,919, filed 22 Jan. 2015; U.S. application Ser. No. 15/375,801, filed 12 Dec. 2016; U.S. application Ser. No. 16/362,444, filed 22 Mar. 2019; and U.S. application Ser. No. 17/033,501, filed 25 Sep. 2020, each of which is incorporated herein in its entirety by this reference.

The system 100 functions to receive and/or process information with which to assess the user's intoxication. Additionally, the system 100 can function to receive and/or process information with which to: detect a user tampering with an alcohol sensing device, determine that a user has not complied with one or more requirements, and/or determine any other information. Further additionally or alternatively, the system 100 can function to provide information to a user (e.g., the user using the device, a remote monitoring entity, etc.) and/or perform any other suitable functions.

The system 100 is preferably configured to perform the method 200 described below, but can additionally or alternatively be configured to perform any other method(s).

3.1 System—Transdermal Alcohol Sensing Device 110

The system 100 includes a transdermal alcohol sensing device no, which functions to collect a set of transdermal alcohol samples from a skin surface of the user to be used in calculating an intoxication metric for the user. Additionally or alternatively, the transdermal alcohol sensing device can function to collect supplementary information associated with an environment of the transdermal alcohol sensing device and/or the user, communicate information to a client application and/or user device, provide information to a remote monitoring entity, and/or can perform any other functions.

Figure 3:
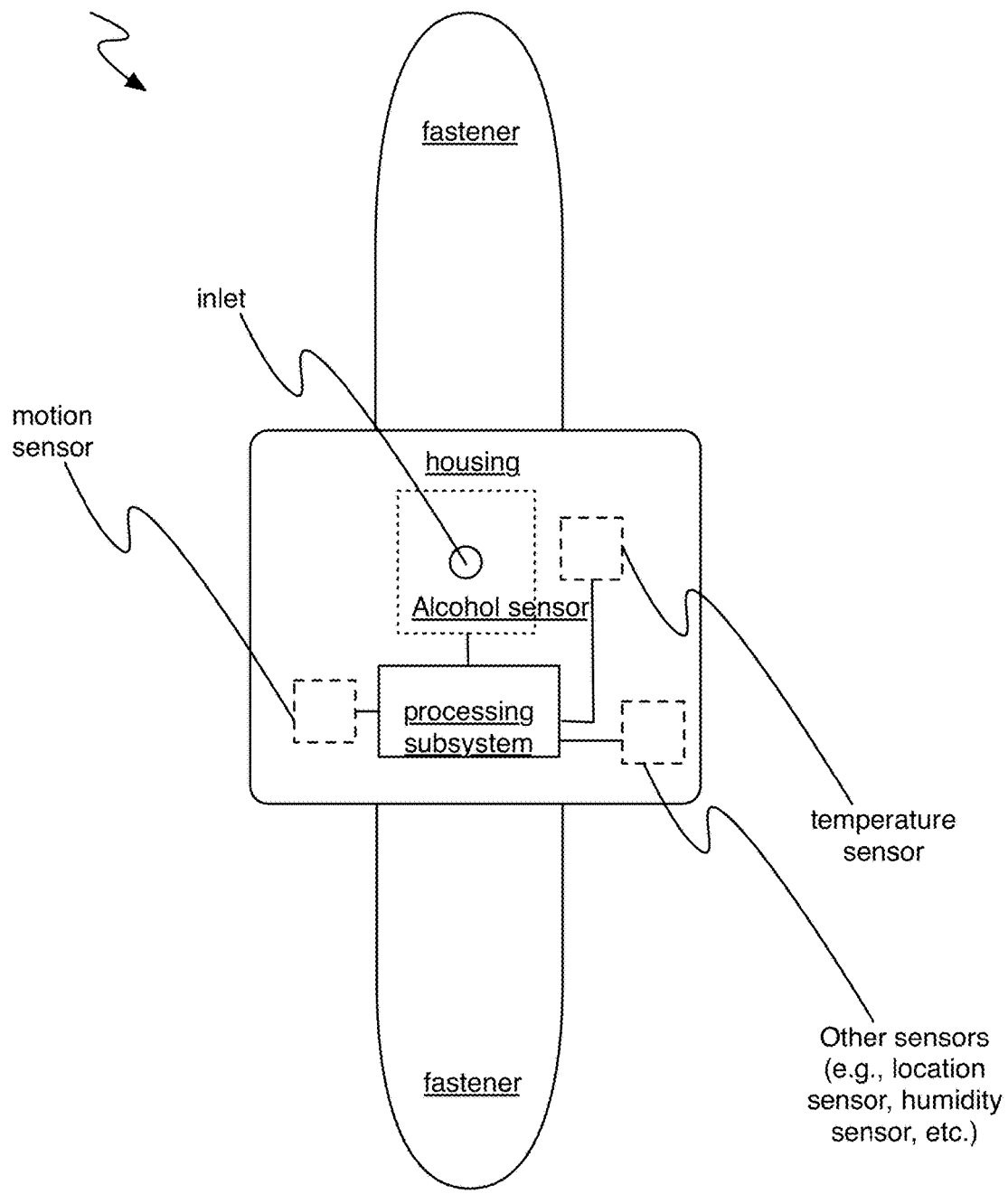
FIG. 3 depicts a variation of a limb-borne (e.g., wrist-borne, ankle-borne, etc.) transdermal alcohol sensing device for remote transdermal alcohol monitoring.
Figure 4A:
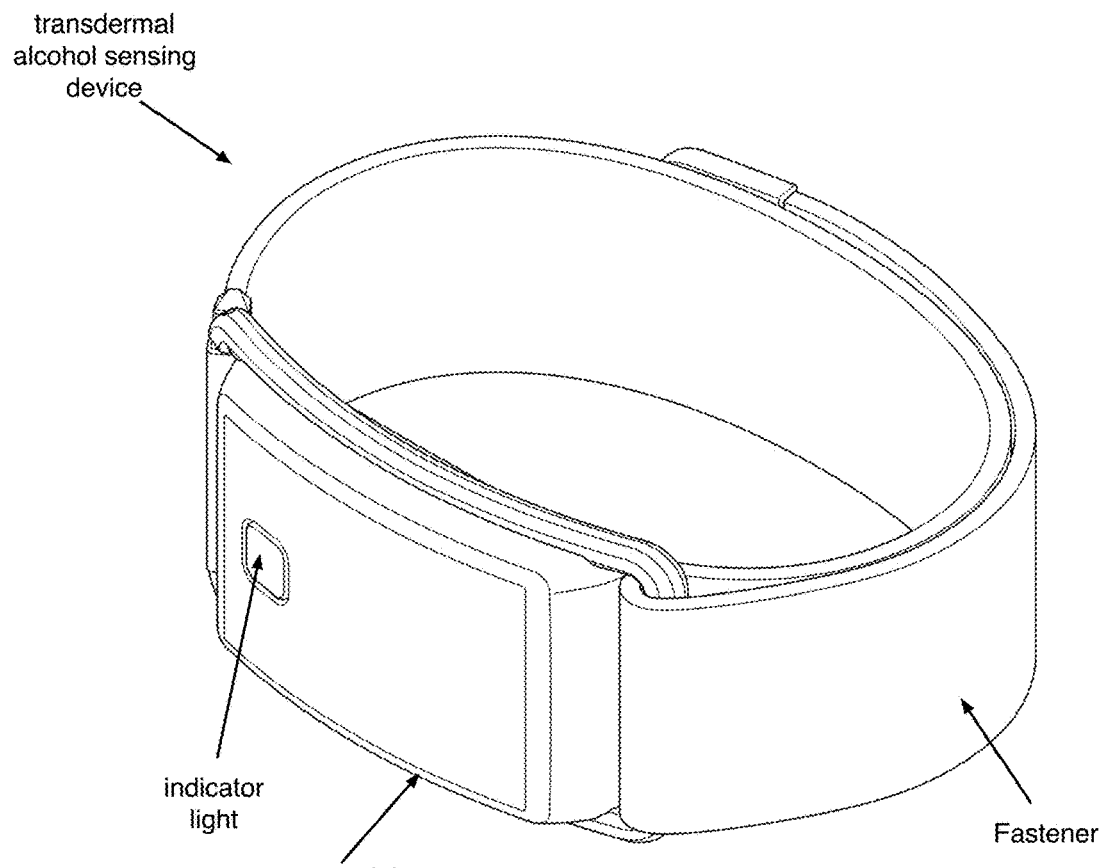
FIGS. 4A-4D depict a variation of a limb-borne (e.g., wrist-borne, ankle-borne, etc.) transdermal alcohol sensing device for remote transdermal alcohol monitoring.
Figure 4B:
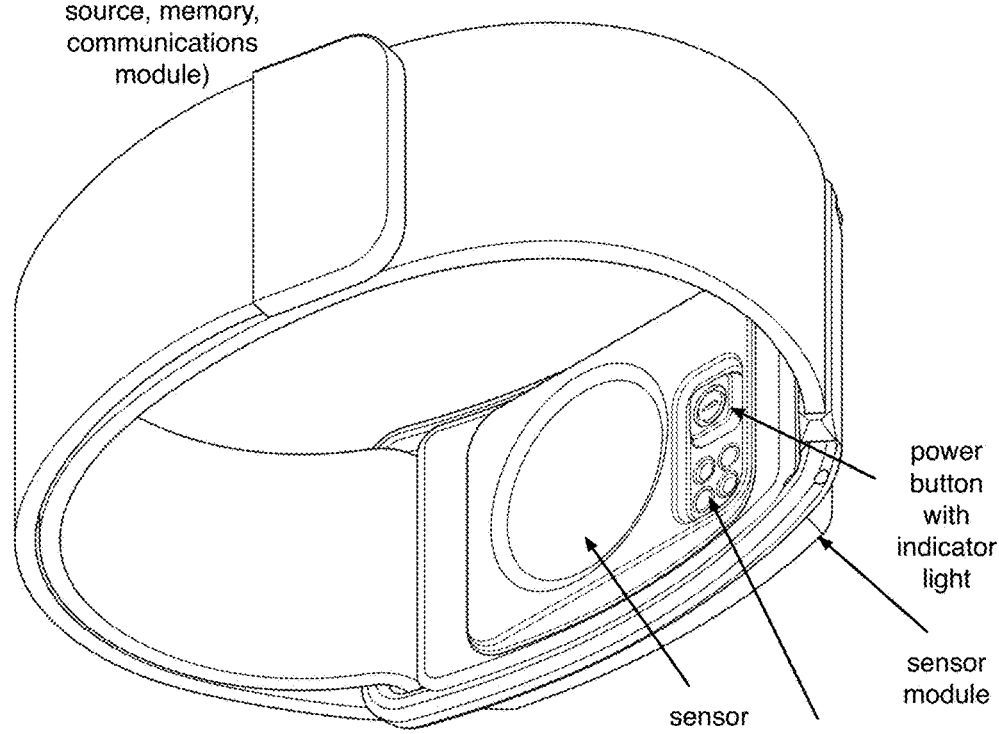
Figure 4C:
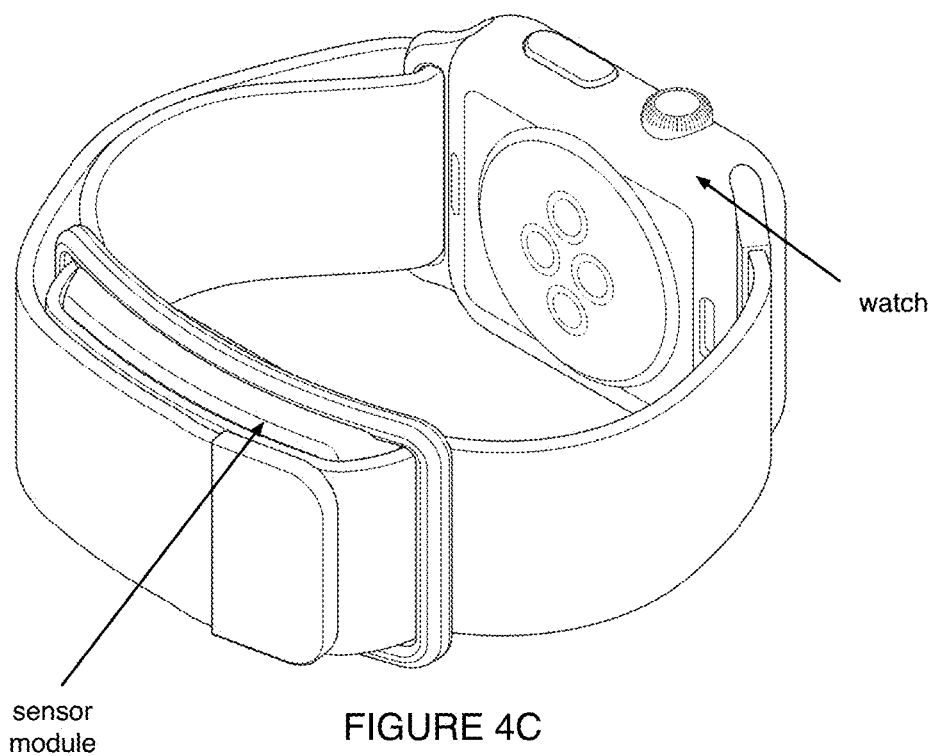
Figure 4D:
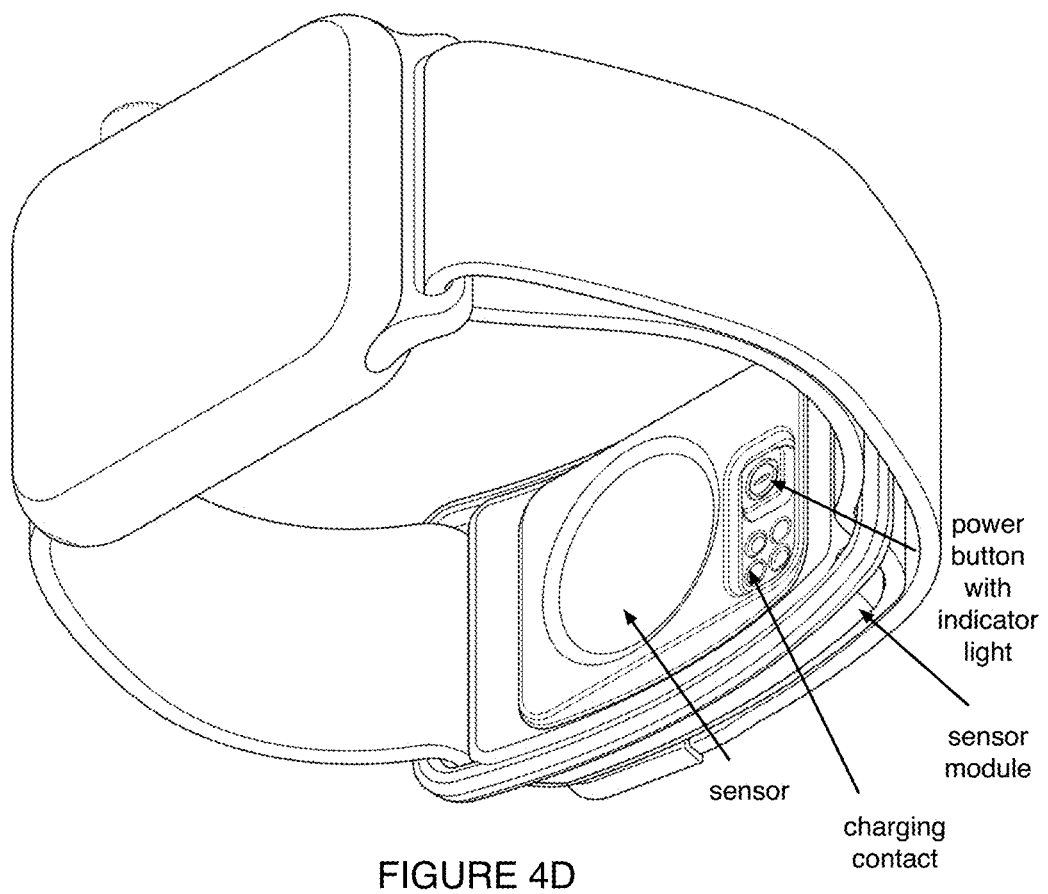

The transdermal alcohol sensing device is preferably a wearable device (e.g., as shown in FIG. 3, as shown in FIGS. 4A-4D, etc.) configured to continuously receive samples from a skin region of the user, such as a wearable wristband which can be worn on a wrist of the user (e.g., with a watch band fastener, with a bracelet fastener, with an adhesive patch, etc.). The wearable device can alternatively be placed on any other region of the body (e.g., ankle, leg, arm, torso, neck, face, stomach, back, hand, foot, etc.), multiple regions, and/or any other regions.

In a preferred set of variations, for instance, the transdermal alcohol sensing device is configured to be worn at a wrist region of the user (e.g., inner wrist region, outer wrist region, side wrist region, circumferential wrist region, etc.), which can function to prevent false positives (e.g., occurring from the accumulation of alcohol and/or alcohol vapor near the ground in bar or other settings), receive robust and/or accurate transdermal intoxication information (e.g., due to the thin layer of skin at the wrist, due to the proximity of veins/arteries in the wrist to the skin's surface, due to the large number and/or volume of veins/arteries in the wrist, etc.), and/or confer any other advantages. In a set of specific examples, the transdermal alcohol sensing device includes a wristband which positions the alcohol sensor at an inner wrist region (e.g., wrist underside) of the user. In other specific examples, the transdermal alcohol sensing device adheres to an inner wrist region of the user. Additionally or alternatively, the transdermal alcohol sensing device can be otherwise arranged proximal to (e.g., fastened to) an inner wrist region of the user, arranged proximal to another wrist region (e.g., outer wrist region) of the user, arranged proximal to a non-wrist region of the user, arranged at multiple locations on and/or near the user, and/or otherwise suitably arranged.

Additionally or alternatively, the transdermal alcohol sensing device can be a handheld device, a tabletop device, another non-wearable device, and/or any other device.

The transdermal alcohol sensing device preferably includes a set of one or more alcohol sensors, which functions to collect a transdermal sample (e.g., perspiration, vapor, sweat, etc.) from a skin surface of a user (the user providing the transdermal alcohol sample equivalently referred to herein as the monitored user) and determine a transdermal alcohol signal based on the transdermal sample. The transdermal alcohol signal can be used as and/or used to determine an intoxication metric.

The alcohol sensor is preferably a fuel cell sensor, but can additionally or alternatively include any or all of: a semiconductor sensor, an enzymatic sensor, and/or any other sensor or combination of sensors.

A semi-permeable membrane can optionally be arranged between the alcohol sensor and the skin surface of the user, which can function to: filter out large particles from contacting the sensor, protect the sensor from damage and/or wear-and-tear, facilitate collection of vapor from the user, and/or provide any other advantages. Alternatively, the transdermal alcohol sensing device can be absent of a semi-permeable membrane, include a different membrane, and/or be otherwise arranged relative to the user.

The transdermal alcohol sensing device preferably includes and/or interfaces with a set of supplementary sensors, wherein the set of supplementary sensors functions to collect supplementary information associated with the user and/or his or her environment. This supplementary information can be used to supplement the transdermal alcohol signal in assessing an intoxication metric of the user; verify the transdermal alcohol signal; detect that a user has tampered with, potentially tampered with, and/or removed the transdermal alcohol sensing device; detect that a user has provided a faulty or fraudulent sample; detect a location at which the user provides a sample; determine lifestyle patterns and/or schedules associated with the user (e.g., body temperature throughout the day, motion throughout the day, times at which user is sleeping vs. awake, times when user is at work vs. at home, etc.); and/or can perform any other suitable functions.

The set of supplementary sensors is preferably at least partially arranged onboard the transdermal alcohol sensing device, but can additionally or alternatively be arranged remote from (e.g., separate from, offboard, etc.) the transdermal alcohol sensing device. These can be arranged, for instance, at any or all of: onboard a user device (e.g., part of the user's smartphone), onboard a supplementary alcohol sensing device, in an environment of the user (e.g., environmental sensors in communication with the user device and/or a client application of the user device, environmental sensors in communication with the transdermal alcohol sensing device, etc.), associated with a $3^{rd}$ party client application executing on the user device, and/or can be otherwise arranged.

The set of supplementary sensors can optionally include a motion sensor (equivalently referred to herein as a movement sensor), which functions to collect motion information (e.g., velocity, speed, acceleration, orientation, etc.) associated with the transdermal alcohol sensing device and/or the user (e.g., in the case of a wearable transdermal alcohol sensing device).

The motion information can be used for any or all of: detecting if a user is moving, detecting if a user is not moving, detecting if a user is slightly moving, determining if and/or detecting that a user is tampering with the transdermal alcohol sensing device, and/or any other motion information.

The motion sensor preferably includes an accelerometer, but can additionally or alternatively include any or all of: a gyroscope, a magnetometer, an inertial measurement unit, an absolute orientation sensor, and/or any other sensors.

In a preferred set of variations, the transdermal alcohol sensing device includes an accelerometer configured to collection motion information from the user, wherein the motion information is used to determine a level of movement associated with the user.

The set of supplementary sensors further preferably includes a temperature sensor, which functions to collect temperature information associated with the user and/or an environment of the transdermal alcohol sensing device. In preferred variations involving a wearable transdermal alcohol sensing device with an alcohol sensor placed at a skin surface of the user, the temperature sensor is preferably placed proximal to the user's skin (e.g., touching the user's skin, proximal to the alcohol sensor, etc.) such that the temperature sensor is measuring a temperature of the user's skin. Additionally or alternatively, the temperature sensor can be otherwise arranged (e.g., opposing a skin surface of the user, at a user device, in an environment of the user, proximal to a skin surface, etc.) and/or configured to detect other temperatures (e.g., temperature of the user's environment).

The temperature information is preferably used to determine the temperature proximal to the alcohol sensor, which can subsequently be used to determine any or all of: whether or not the transdermal alcohol sensing device has been tampered with (e.g., the alcohol sensor covered to try to block alcohol samples from being collected at the alcohol sensor), the temperature of the environment that the transdermal alcohol sensing device has been placed within, and/or any other information.

The temperature sensor can include any or all of: a thermistor, a thermocouple, a resistive temperature measuring device, an infrared sensor, a thermometer, an infrared sensor, a bimetallic device, a silicon diode, and/or any other sensor(s).

Additionally or alternatively, temperature information can be collected from a supplementary device (e.g., an Apple watch of the user), from a $3^{rd}$ party client application, and/or any other information sources.

Additionally or alternatively, the set of supplementary sensors can include any other sensors, a clock, and/or other components.

The transdermal alcohol sensing device can optionally include one or more tamper-resistant and/or tamper-detection components, which function to: prevent the user from tampering with (e.g., removing, breaking, etc.) the transdermal alcohol sensing device; detect if and/or when a user has potentially removed and/or adjusted the transdermal alcohol sensing device; and/or perform any other functions. As such, the tamper-resistant and/or tamper-detection component is preferably arranged onboard the transdermal alcohol sensing device and can include any or all of: a locking mechanism (e.g., lock coupled to a fastener); an adjustment detection mechanism (e.g., to detect if a fastener associated with the transdermal alcohol sensing device has changed size settings); and/or any other components. In some variations, for instance, the transdermal alcohol sensing device includes and/or interfaces with any or all of the components as described in U.S. application Ser. No. 17/033,501, filed 25 Sep. 2020, which is incorporated herein in its entirety by this reference.

Additionally or alternatively, the tamper-resistant/tamper-detection component can include and/or interface with any or all of the supplementary sensors described above (e.g., temperature sensor, motion sensor, etc.), the alcohol sensor, and/or any other sensors.

Further additionally or alternatively, any or all of the tamper resistance and/or tamper detection can be implemented through the mobile user device and/or client application, such as through any or all of: video recordings of the user wearing the transdermal alcohol sensing device (e.g., as provided to the probation officer, as analyzed with computer vision processes, etc.), detecting that the mobile user device is within range of the transdermal alcohol sensing device, through sensors onboard the mobile user device, and/or with any other components or processes.

The transdermal alcohol sensing device can optionally include any other components, such as, but not limited to, any or all of: a processing subsystem (e.g., to determine a signal from the sample), a communication subsystem (e.g., to wirelessly communicate with the user device and/or any other devices), a power source, and/or any other components.

In a first variation, the transdermal alcohol sensing device includes an alcohol sensor, a temperature sensor, and a motion sensor, which are individually and/or collectively configured for any or all of: detecting an intoxication metric (e.g., TAC, BAC, etc.) associated with the user, detecting that a user has tampered with the transdermal alcohol sensing device, and/or any other functions. The transdermal alcohol sensing device further preferably includes a processing subsystem (e.g., onboard the transdermal alcohol sensing device), a power source (e.g., rechargeable battery), a communication interface (e.g., Bluetooth module, Wifi module, etc.), and/or any other components. The alcohol sensor can optionally be arranged proximal to a permeable membrane, where the permeable membrane is arranged between the alcohol sensor and the user when the device is coupled to the user (e.g., where the alcohol sensor is arranged within a cavity). Additionally or alternatively, the transdermal alcohol sensing device can include any other sensors or components arranged in any suitable configuration.

In a first specific example, the transdermal alcohol sensing device is configured to be worn at a wrist region of the user, such as with any or all of: a wristband form factor (e.g., where the transdermal alcohol sensing device can be fastened to a circumference of the user's wrist); an adhesive form factor; and/or any other form factors.

In a second specific example, the transdermal alcohol sensing device is configured to be worn at another region of the user (and/or at multiple regions of the user), such as, but not limited to: a user's ankle, a user's leg, a user's arm, a user's torso, a user's neck, a user's head, a user's back, a user's hand, a user's finger, a user's foot, and/or any other regions.

In a second variation, additional or alternative to the first, the transdermal alcohol sensing device includes a tamper detection/prevention component, which functions to detect that user has removed and/or is attempting to remove or otherwise manipulate (e.g., break, prevent from taking measurements, etc.) the transdermal alcohol sensing device.

Additionally or alternatively, any or all of the tamper detection and/or prevention can be determined based on the supplementary sensors and/or the alcohol sensor.

Additionally or alternatively, the transdermal alcohol sensing device can include any other suitable components.

3.2 System—User Device 120

The system 100 preferably interfaces with a user device 120, which functions to receive and optionally process and/or transmit (e.g., to a remote computing system, to a remote monitoring entity, etc.) information collected at the transdermal alcohol sensing device. Additionally or alternatively, the user device 120 can receive and/or process information collected from a supplementary alcohol sensing device and/or other devices; collect information at a set of supplementary sensors; transmit information to a remote computing system and/or user interface; receive inputs from a user; host a client application which any or all of the users can access; and/or can perform any other functions.

The user device is preferably a mobile user device (e.g., mobile relative to the user, mobile relative to the transdermal alcohol sensing device, etc.), but can additionally or alternatively include a stationary device (e.g., fixed to the transdermal alcohol sensing device, fixed to the user, fixed to a home of the user, large and/or otherwise difficult to move such as a desktop computer, etc.), and/or any combination of devices.

Figure 7:
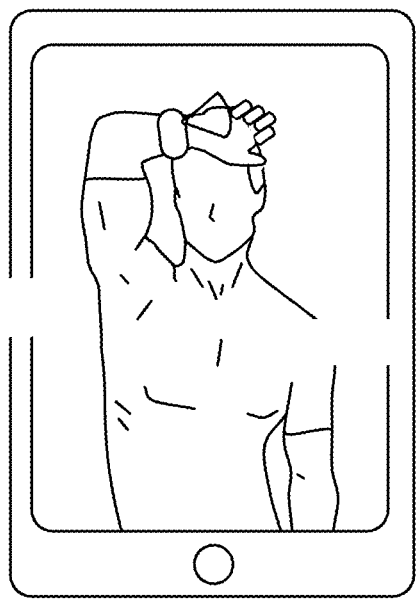
FIG. 7 depicts an illustrative example of a monitored user's video feed.
Figures 8A, 8B:
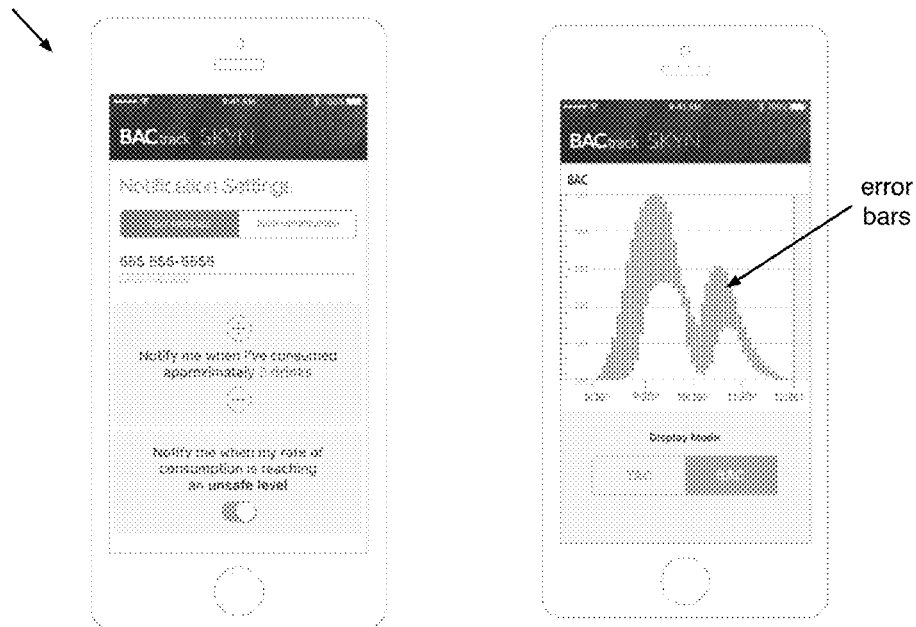
FIGS. 8A-8D depict an illustrative example of various information which can be portrayed to a user at a client application.
Figures 8C, 8D:
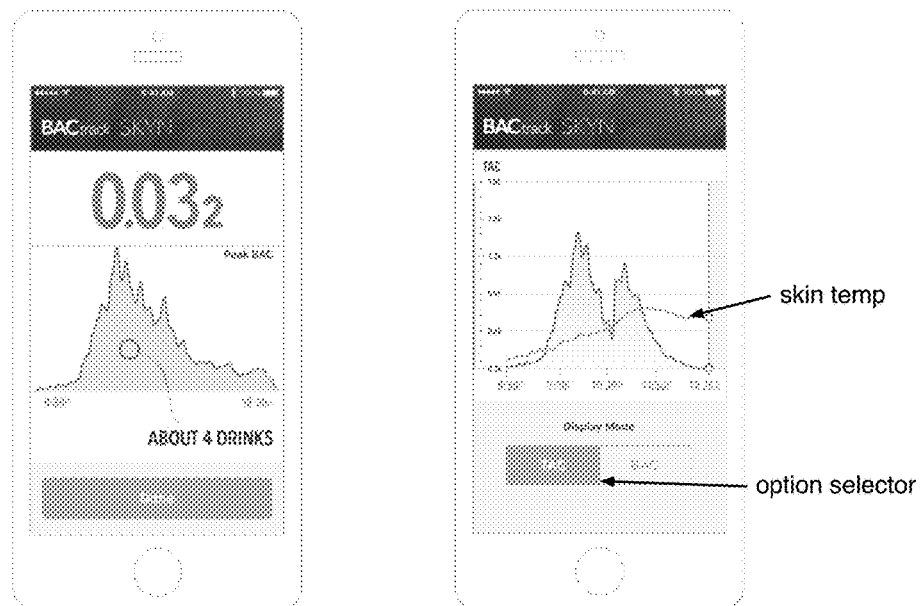
Figure 9A:
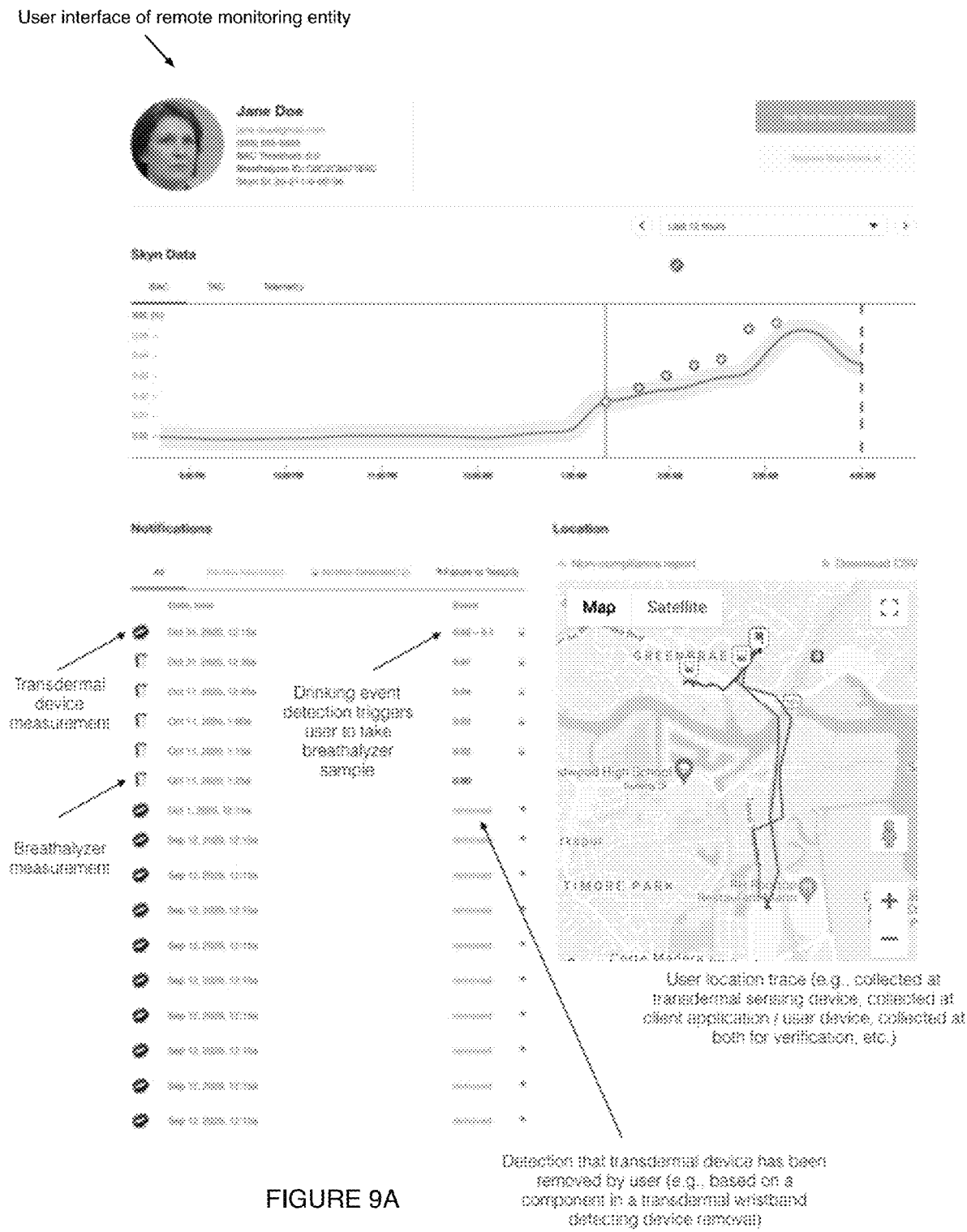
FIGS. 9A-9I depict illustrative examples of a user interface displaying information associated with a set of monitored users to a remote monitoring entity.
Figure 9B:
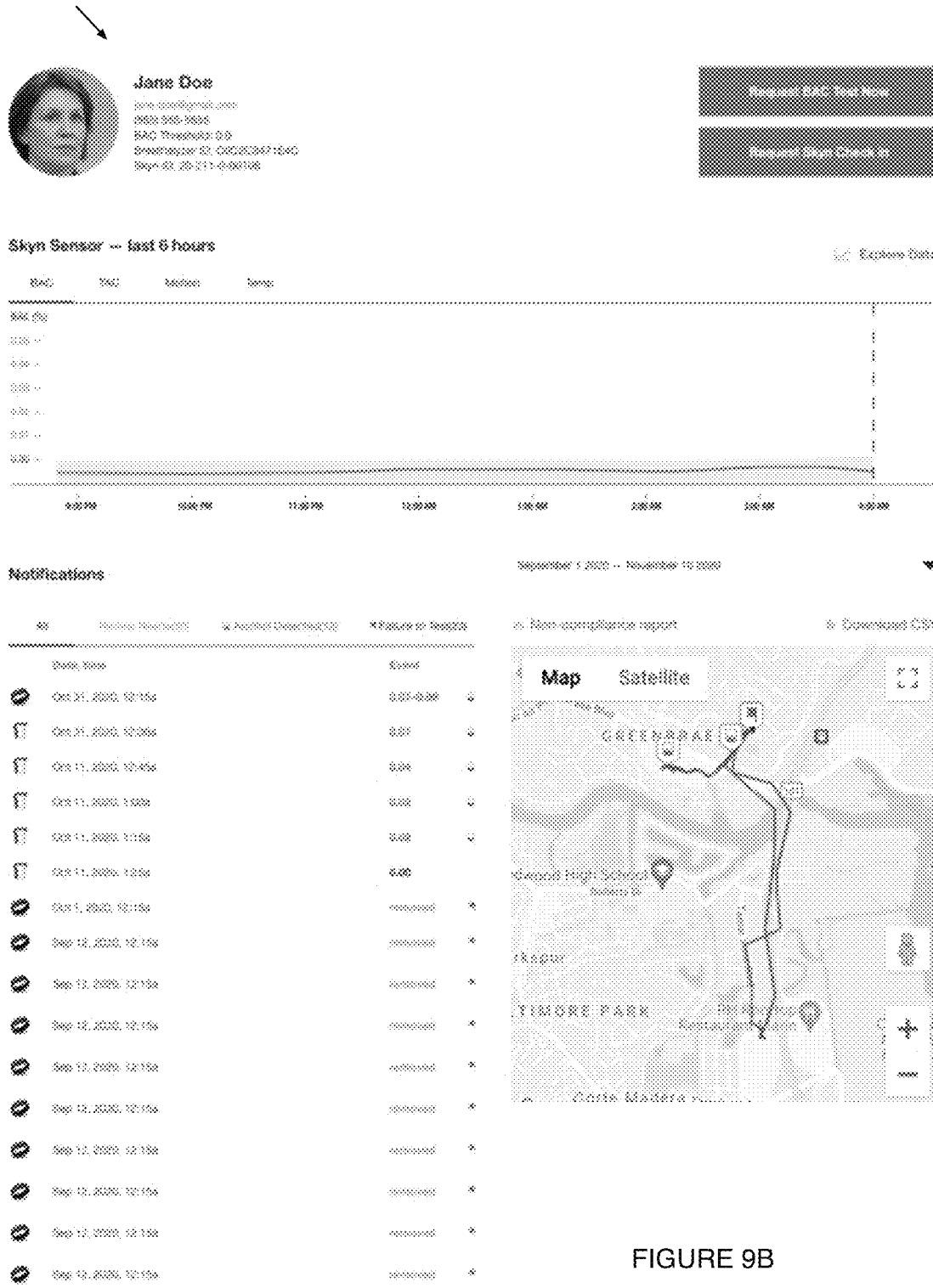
Figure 9C:
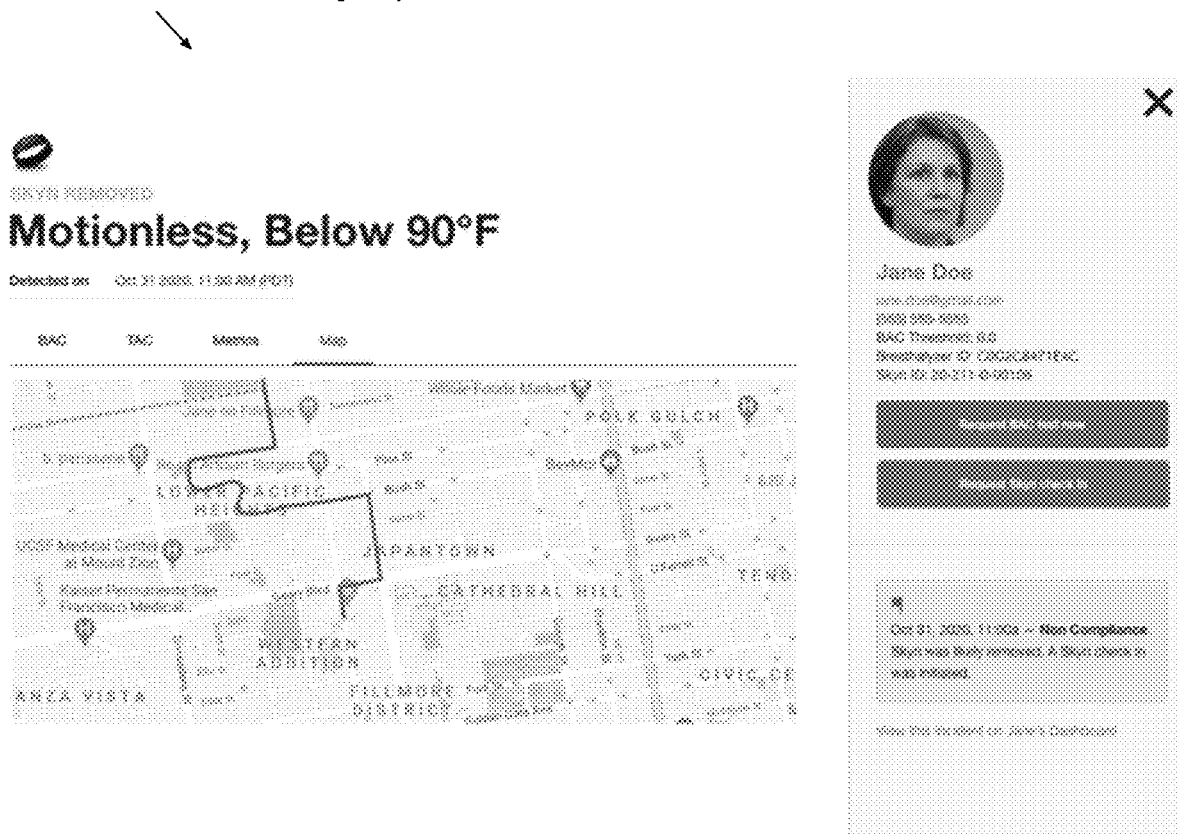
Figure 9D:
Figure 9E:
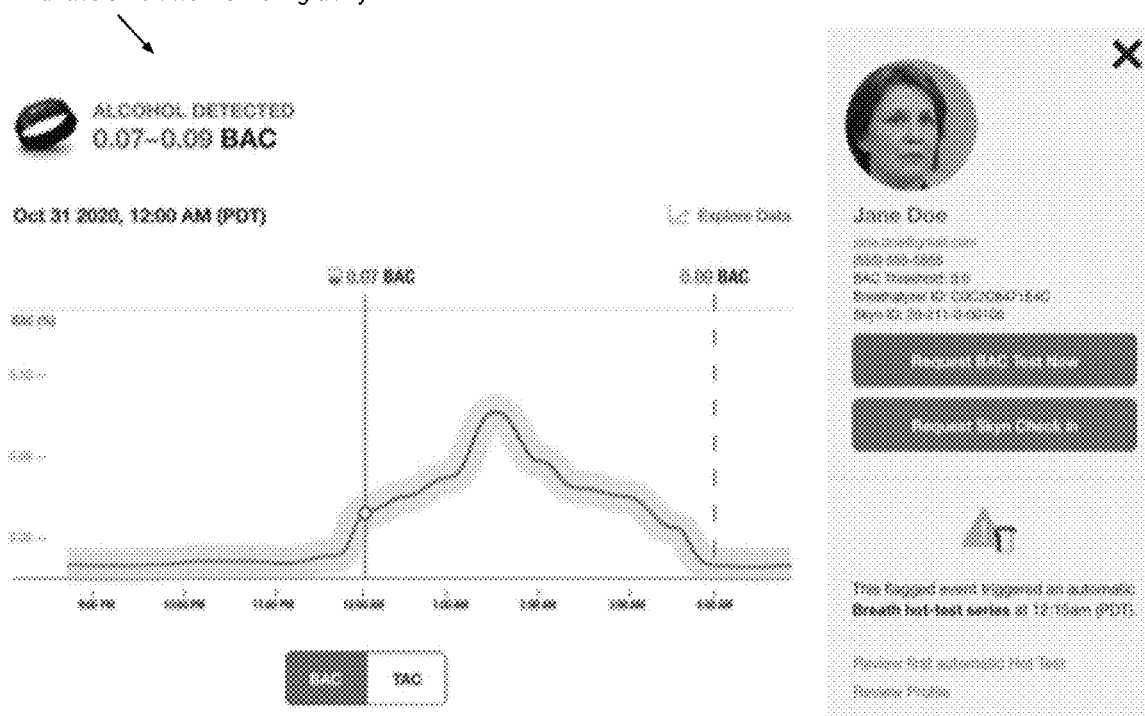
Figure 9F:
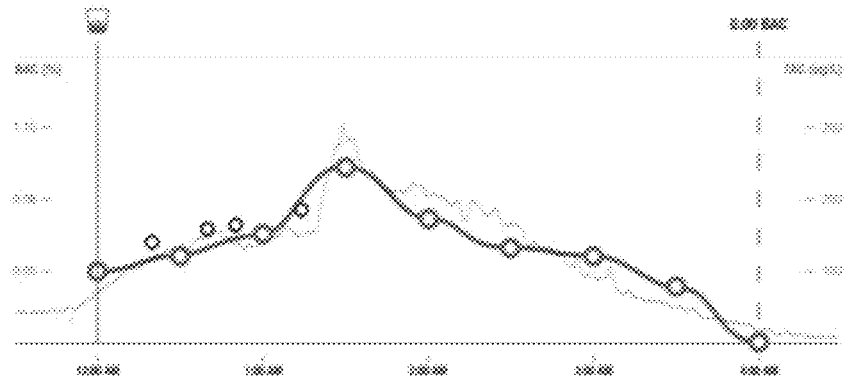
Figure 9F:
Figure 9G:
Figure 9H:
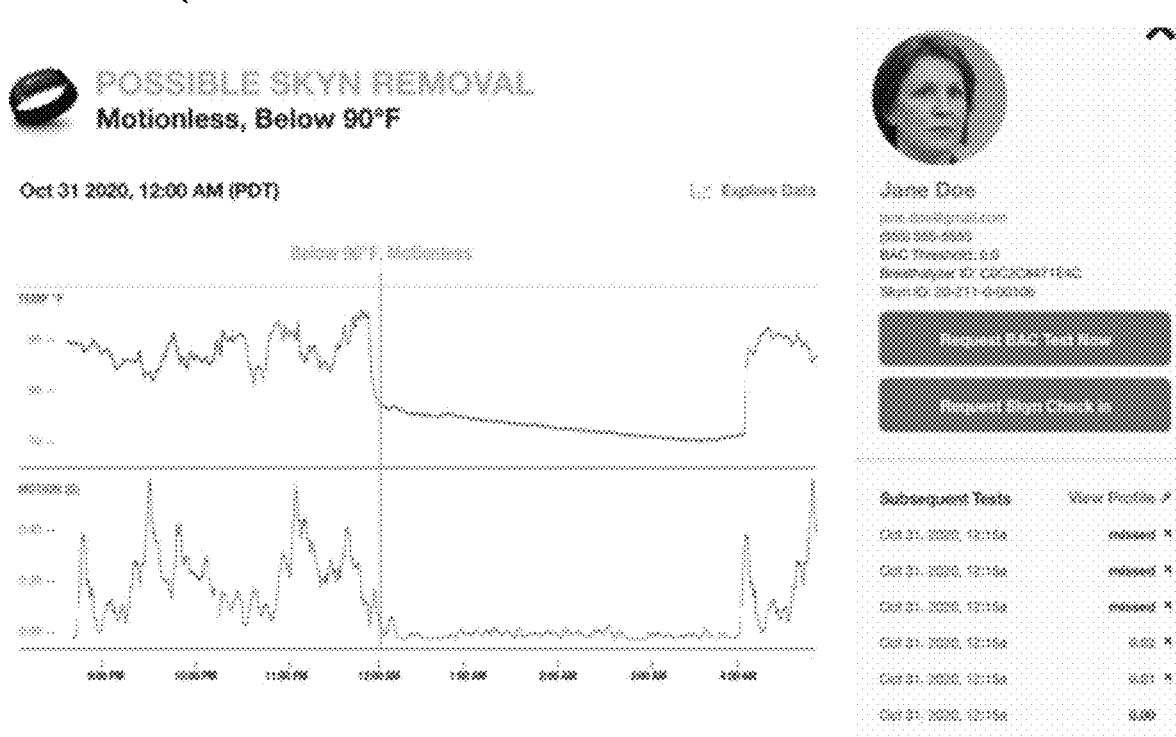
Figure 9I:
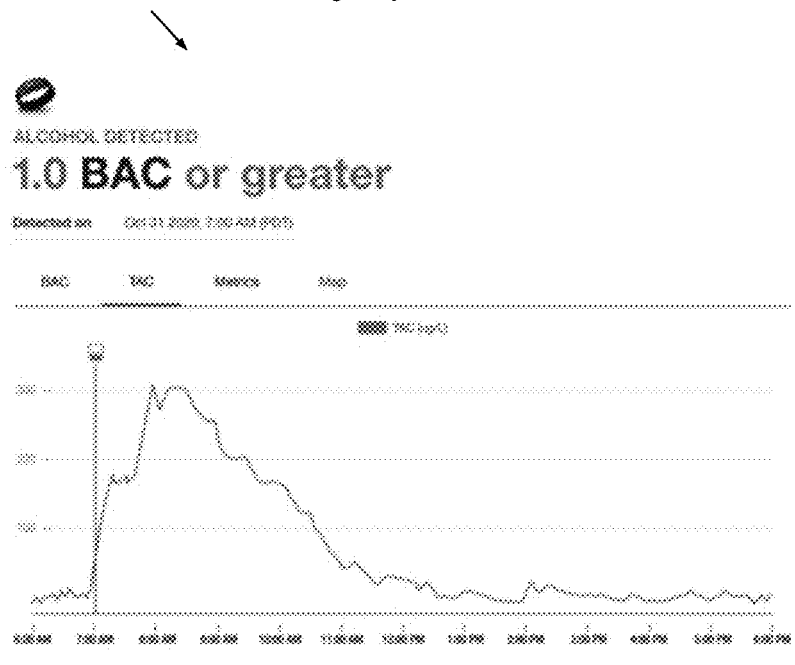
Figure 9I:
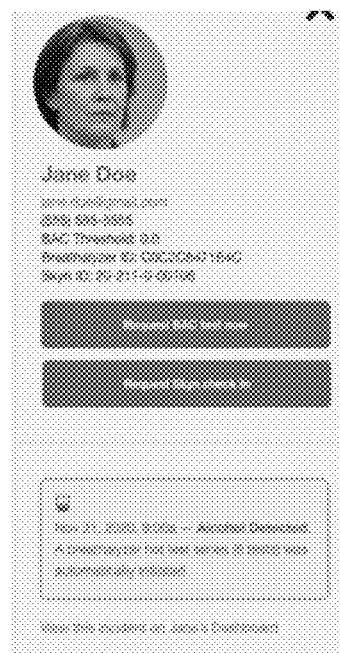

The user device preferably includes and/or interfaces with (e.g., hosts) a client application, wherein the client application functions to communicate information (e.g., notifications, alerts, etc.) to a user interacting with the transdermal alcohol sensing device and optionally to any other users (e.g., probation officer, remote monitoring entity, etc.). Additionally or alternatively, the client application can function to interface with $3^{rd}$ party client applications at the user device, enable video conferencing between users, enable video recording of the monitored user (e.g., for verification, authentication, as shown in FIG. 7, etc.), process any or all of the set of inputs, and/or can provide any other functionality.

The user device is preferably a personal device (equivalently referred to herein as a user device) of the monitored user, but can additionally or alternatively be a $3^{rd}$ party device, a prescribed device (e.g., by a remote monitoring entity), and/or any other device.

Examples of the user device include a tablet, smartphone, mobile phone, laptop, watch, wearable device (e.g., glasses), or any other suitable user device. The user device can include power storage (e.g., a battery), processing systems (e.g., CPU, GPU, memory, etc.), user outputs (e.g., display, speaker, vibration mechanism, etc.), user inputs (e.g., a keyboard, touchscreen, microphone, etc.), a location system (e.g., a GPS system), sensors (e.g., optical sensors, such as light sensors and cameras, orientation sensors, such as accelerometers, gyroscopes, and altimeters, audio sensors, such as microphones, etc.), data communication system (e.g., a WiFi module, Bluetooth module, BLE, cellular module, etc.), or any other suitable component The user device can optionally include any or all of the set of supplementary sensors (e.g., temperature sensor, motion sensor, etc.). In some variations, for instance, location information is collected from the user device through one or more GPS sensors arranged onboard the user device. The GPS data preferably functions to track a location of the user, which can be used by a remote monitoring entity to monitor where the user has traveled to.

In some variations, for instance, the remote monitoring entity has implemented and/or assigned inclusion and exclusion zones for the user, which can then be compared with location information collected from the user device, where inclusion zones represent regions in which a user is permitted to be located and exclusion zones represent regions in which a user is not permitted to be located. Exclusion zones can include, for instance, any or all of: bars or other establishments which serve alcohol, states which are across state lines from the user's current state of residence, regions which are outside of a predetermined distance threshold from the user's residence, and/or any other regions. Additionally or alternatively, the location information can be collected at the transdermal alcohol sensing device, at another device, and/or at any combination of devices.

The user device can optionally include any or all of: an onboard processing subsystem (e.g., in communication with a processing subsystem onboard the transdermal alcohol sensing device, in absence of a processing subsystem onboard the transdermal alcohol sensing device, etc.), such as any or all of: one or more processors (e.g., microprocessors), one or more controllers (e.g., microcontrollers), one or more computers, and/or any other components.

Additionally or alternatively, the location information can be otherwise used and/or the user device can include any other sensors and/or components.

In a first variation, the user device includes a mobile smartphone device, which is in communication with the transdermal alcohol sensing via a Bluetooth connection.

In a second variation, the user device includes a mobile smartphone device, which is in communication with the transdermal alcohol sensing via a Wifi connection.

In a third variation, the user device includes a mobile smartphone device, which is in communication with the transdermal alcohol sensing via an RF connection.

In a fourth variation, the user device includes a mobile smartphone device, which is in communication with the transdermal alcohol sensing via a wired connection.

Additionally or alternatively, the user device can include any other type of device in communication with the transdermal alcohol sensing device.

3.3 System—Supplementary Alcohol Sensing Device 130

The system 100 can optionally include and/or interface with a supplementary alcohol sensing device (equivalently referred to herein as a second and/or secondary alcohol sensing device), which can function to perform any or all of: validate alcohol data from the transdermal alcohol sensing device, calibrate alcohol data from the transdermal alcohol sensing device, verify and/or authenticate the monitored user, and/or can perform any other functions.

The supplementary alcohol sensing device is preferably a breathalyzer device which determines an intoxication metric based on a breath sample from the user, but can additionally or alternatively include any other alcohol sensing devices.

The supplementary alcohol sensing device is preferably in communication with the user device, further preferably with a client application executable on the user device, but can additionally or alternatively be absent of communication with the user device and/or can be in communication with any or all of: a remote computing system, the transdermal alcohol sensing device, and/or any other components. Alternatively, the second alcohol sensing device can be absent of communication with one or more components of the system (e.g., such that the remote monitoring entity can receive the information directly from the breathalyzer).

The supplementary alcohol sensing device can optionally include any other components.

3.4 System—Other Components

The system 100 can additionally or alternatively include and/or interface with any other components, such as, but not limited to, any or all of: a computing subsystem (e.g., remote computing subsystem, cloud-based computing subsystem, etc.) configured for any or all of the computing of the method 200; a user interface for the remote monitoring entity (e.g., to show metrics and/or sensor data associated with the monitored user(s)) which can be part of or independent from the client application; a user interface for the monitored user which can be part of or independent from the client application; and/or any other components.

In a preferred set of variations, for instance, the system 100 includes a remote computing subsystem (e.g., cloud-based computing subsystem), which functions to collect information from the user device (e.g., via the client application) and/or to transmit information to a device (e.g., user device) associated with a remote monitoring entity.

Examples of information presented at a user interface associated with a remote monitoring entity (e.g., probation officer) are shown in FIGS. 9A-9I.

3.5 System—Variations

In a first variation of the system 100, the system includes a transdermal alcohol sensing device which is configured as a wearable which can be coupled to the user for continuous sampling of perspiration from a skin surface of the user; an alcohol sensor coupled to the transdermal alcohol sensing device and proximal to (e.g., touching, offset from with an inlet, etc.) a skin surface of the user; a set of supplementary sensors (e.g., motion sensor, temperature sensor, etc.) configured to sample information associated with the user; a client application executing on a user device of the user (e.g., as shown in FIGS. 8A-8D), wherein the client application is configured to receive information from the transdermal alcohol sensing device and optionally from sensors (e.g., location sensor) and/or $3^{rd}$ party client applications of the user device, the client application further configured to transmit information to a remote monitoring entity (e.g., via a remote computing subsystem); and optionally a supplementary alcohol sensing device (e.g., breathalyzer), which is also preferably configured to communication alcohol signals (e.g., BAC signals) to the client application, and can be used as a supplementary alcohol signal and/or for verification of the user. Additionally or alternatively, the system 100 can include any other suitable components.

In a specific example, the transdermal alcohol sensing device is configured to be worn on a limb of the user (e.g., wrist, ankle, etc.) and includes a transdermal alcohol sensor, a motion sensor, a temperature sensor, and a Bluetooth (e.g., BLE) module configured to communicate the sensor information to a client application executing on a user device of the user.

4. Method 200

As shown in FIG. 2, a method 200 for remote transdermal alcohol monitoring includes: receiving a set of inputs S210; determining a set of outputs S220; and triggering an action based on the set of outputs S230. Additionally or alternatively, the method 200 can include and/or interface with any or all of the processes, methods, embodiments, and/or examples as described in any or all of: U.S. application Ser. No. 14/169,029, filed 30 Jan. 2014; U.S. application Ser. No. 14/602,919, filed 22 Jan. 2015; U.S. application Ser. No. 15/375,801, filed 12 Dec. 2016; U.S. application Ser. No. 16/362,444, filed 22 Mar. 2019; and U.S. application Ser. No. 17/033,501, filed 25 Sep. 2020, each of which is incorporated herein in its entirety by this reference, or any other suitable processes performed in any suitable order.

The method 200 is preferably performed with a system 100 as described above, but can additionally or alternatively be performed with any other suitable system.

The method 200 functions to monitor an intoxication of a user through the collection of transdermal alcohol samples. The method 200 further preferably functions to provide reliable alcohol monitoring capability to a remote entity associated with the user (e.g., a parole officer, a criminal justice group, a friend, an accountability partner, etc.). Additionally or alternatively, the method 200 can function to handle inconsistencies involved in receipt of data from the transdermal alcohol sensing device and/or from the client application (e.g., to a remote computing system), and/or can perform any other function(s).

In a set of examples, the method 200 functions to enable a remote monitoring entity (e.g., probation officer, contact of user, family member of user, friend of user, doctor or therapist of user, alcohol addiction counselor, etc.) to react quickly in an event that alcohol is detected in the user's body, in an event that the user is predicted to take part in a drinking event (e.g., has a location at or approaching a bar), in an event that the user is determined or predicted to be tampering with a transdermal device or otherwise not complying with intoxication monitoring, and/or in any other events. Enabling the remote monitoring entity to act quickly is preferably enabled through the frequent collection and analysis of information (e.g., sensor data received at the transdermal device) and can include any or all of: a remote monitoring entity (e.g., probation officer) checking in on the user (e.g., driving to the user's location, initiating a phone call and/or video call with the user, requiring a breathalyzer or other supplementary test, etc.), a remote monitoring entity attempting to prevent the user from taking part in a drinking event (e.g., alcohol abuse counselor messaging the user if it is suspected that the user make take part in a drinking event), a remote monitoring entity adjusting the user's program (e.g., enforcing that the user wear a tamper-proof version of the device in an event that the user attempts tampering, narrowing the user's allowed locations, etc.), and/or any other actions.

The method 200 further preferably functions to detect if and when a user has tampered with (e.g., removed, altered, broken, etc.) the transdermal alcohol sensing device (e.g., and to trigger an appropriate action upon detection). In specific examples, this is performed through the processing of sensor data collected at the transdermal alcohol sensing device. Additionally or alternatively, sensor data from sensors offboard the transdermal alcohol sensing device (e.g., user device sensors, supplementary alcohol sensing device sensors, etc.) can be used. Further additionally or alternatively, a tamper-detection/tamper-resistant component of the transdermal alcohol sensing device can be used.

Additionally or alternatively, the method 200 can perform any other function(s).

In preferred variations, the method 200 is configured to operate in accordance with inconsistent and/or infrequent background syncing associated with the operating system (e.g., iOS) of the user device hosting the client application, which can cause inconsistencies in any or all of: the frequency at which information is received at the client application from the transdermal alcohol sensing device; the frequency at which information is received at a remote computing system (e.g., the cloud) from the client application; the frequency at which information is received at the user device from the client application; and/or any other information transmission (e.g., the frequency at which information is received at the client application from the supplementary alcohol sensing device). In some use cases, for instance, background syncing of the operating system is associated with relatively high variability (e.g., on average syncing occurs every 10 minutes but with +/−2 minute variability) in normal daytime conditions, but can degrade precipitously in certain circumstances, such as any or all of: a low battery mode of the user device (e.g., less than 20% battery), an overnight charging mode or other charging mode, a nighttime mode, a usage of high-power-consumption $3^{rd}$ party applications (e.g., foregrounding of high-power-consumption $3^{rd}$ party applications), and/or any other scenarios. In additional or alternative use cases, the frequency at which information is received at a remote computing system (e.g., cloud) from the user device (e.g., from the client application executing/operating on the user device) (and/or the frequency at which the information is received at the user device from the transdermal device) is on average lower than the frequency at which data is sampled at the sensors of the transdermal alcohol sensing device. In specific examples, for instance, the frequency at which information is received at the remote computing system (and/or the frequency at which information is received at the user device from the transdermal device) is on average greater than 1 minute (e.g., between 1 minute and 20 minutes, between 1 minute and 5 minutes, between 5 minutes and 10 minutes, between 10 minutes and 15 minutes, between 15 minutes and 20 minutes, greater than 20 minutes, between 10 minutes and 20 minutes, any interval between 1 minute and 20 minutes, etc.) whereas the frequency at which data is sampled at the transdermal device (and/or at which data is received at the client application) is on average less than 1 minute (e.g., every 20 seconds, every 10 seconds, every 5 seconds, between every second and every 5 seconds, between every 5 seconds and every 15 seconds, between every 15 seconds and every 25 seconds, between every 20 and 40 seconds, between every 30 seconds and every minute, etc.). Additionally or alternatively, the frequencies can be the same, the frequency at which information is received at a remote computing system (e.g., cloud) from the user device (e.g., from the client application executing/operating on the user device) is on average higher than the frequency at which data is sampled at the sensors of the transdermal alcohol sensing device, the frequencies can vary, and/or the frequencies can be otherwise valued.

In these use cases, the transdermal alcohol sensing device is still sampling and/or recording data (e.g., and storing it at the transdermal alcohol sensing device, and transmitting it to the user device/client application, etc.), but is not receiving it at the remote computing system (and/or the user device/client application) and therefore not able to receive it for processing (e.g., at a cloud computing system, at the user device, etc.) and/or transmit it to a remote monitoring entity for monitoring. In other conventional client applications, this typically does not pose as an issue, and the application can simply sync when it is foregrounded (and/or irregularly), since the user is the only person concerned about the data. However, in the case of remote monitoring (e.g., for criminal justice), the remote user needs to be able to access the data (e.g., routinely, robustly, continuously, etc.).

As such, the method 200 is preferably configured (e.g., through any or all of the actions triggered in S230) to account for and/or adapt to these inconsistencies.

Additionally or alternatively, data can be sent to the remote computing system at regular intervals, without interruption, at high frequencies (e.g., the same as that in which data is sampled at the transdermal device), and/or at any other times.

Additionally or alternatively, the method 200 can be otherwise suitably configured.

4.1 Method—Receiving a Set of Inputs S210

The method 200 includes receiving a set of inputs S210, which functions to receive information with which to perform any or all of the remaining processes of the method 200.

S210 is preferably performed initially in the method 200 and further preferably continuously throughout the monitored user's use of the transdermal alcohol sensing device. Additionally or alternatively, any or all of S210 can be prompted in response to a trigger (e.g., prompting S216 in response to S230) and/or performed at any other times.

S210 preferably includes receiving a set of body samples from the region or regions of the user using the transdermal alcohol sensing device S212, which functions to receive alcohol samples with which to determine an intoxication metric (e.g., transdermal alcohol concentration [TAC], blood alcohol concentration [BAC] based on a TAC to BAC conversion, etc.). The samples are preferably received from an alcohol sensor as described above, but can additionally or alternatively be received from any other sensors.

Additionally or alternatively, any or all of the body samples can be used to detect that the user has tampered with the transdermal alcohol sensing device (and/or that the user is not using the device properly). In some variations, for instance, the collected body samples include alcohol information (e.g., ethanol particles, ethanol concentrations, etc.) as well as information associated with other particles and/or molecules and/or compounds and/or materials, such as molecules related to ethanol or others. The signal determined based on these body samples is typically non-zero and/or shows variation from sample-to-sample (e.g., indicating noise from the ethanol-related molecules), even when the user is not drinking (e.g., just by nature of the alcohol sensor collecting samples from the user's body). In an event that the user has tampered with the device—such as by removing the device (e.g., and placing it on an object) and/or covering the alcohol sensor (e.g., with a film, plastic, cardboard, clothing, etc.), either on purpose or by accident—a change in this baseline signal (e.g., collapsed to zero, no longer varying as normal, etc.) can indicate that the device has been removed and/or tampered with. Additionally or alternatively, this baseline signal can serve as a user-specific signature (e.g., reflecting the user's particular body chemistry), where if it is detected that this baseline signal changes, it can be determined that the user has placed his device on another user (e.g., if the main user has been drinking).

In a preferred set of variations, for instance, the set of body samples includes vapor/sweat/air samples from a skin surface (e.g., the wrist) of the user which are used to determine a TAC value (e.g., which is then subsequently used to determine a BAC value in subsequent processes of the method) and/or other intoxication metric of the user.

Additionally, the set of body samples can further detect a baseline signal associated with the user, which can be used to determine and/or predict (e.g., with other signals from supplementary sensors) that the user has tampered with the transdermal device.

S210 further preferably includes receiving information from a set of supplementary sensors S214, such as, but not limited to, any or all of the supplementary sensors described above, which functions to receive supplementary information such as any or all of: motion information, temperature information, time information, location information, and/or any other suitable information. This can, in turn, be used to determine any or all: one or more schedules and/or patterns associated with the user (e.g., when the user is at work vs. at home based on location data, when and/or how often the user exercises, when the user sleeps based on motion and/or temperature data, etc.); if and/or when the user has tampered with the transdermal device (e.g., based on the transdermal device detecting no motion for a at least a predetermined period of time, based on the transdermal device detecting a temperature which is different than [e.g., less than] an average body temperature and/or a particular body temperature of the user, based on detecting that the transdermal device is at a different location than that of the user device, etc.); and/or can be used to determine any other information.

Additionally or alternatively, any or all of the sensor information can be used to trigger one or more actions (e.g., as described below).

Further additionally or alternatively, any or all of the sensor information can be used to determine and/or adjust an intoxication metric calculated for the user (e.g., to adjust its value if the user is in a particularly hot environment, to adjust the value if the user has been exercising, etc.).

The sensor information can be collected from any or all of: the transdermal alcohol sensing device, the user device, a supplementary alcohol sensing device, a third party device, a server and/or remote computing system, and/or any combination of sources.

S210 can optionally include receiving a set of samples from a supplementary alcohol sensing device S216, which functions to receive other alcohol samples with which to determine a second intoxication metric (e.g., BAC directly). S216 is preferably triggered in response to S230, but can additionally or alternatively be triggered in accordance with a schedule (e.g., once per week), randomly, and/or at any other times.

S210 can optionally include receiving user information, which can be used to: calibrate and/or normalize any or all of the alcohol samples and/or supplementary information (e.g., based on a user's sex, based on a user's weight, based on a user's age, based on the climate of the user's residence, etc.); determine a schedule of the user (e.g., his or her sleeping schedule, his or her work schedule, etc.); determine exclusion and/or inclusion zones associated with the user; determine a level of risk associated with the user; and/or be otherwise used. Additionally or alternatively, any or all of the user information can be determined (e.g., based on sensor information, based on user input at the client application, etc.) and/or predicted (e.g., with a set of machine learning models, with a set of trained models, with a set of deep learning models, etc.).

S210 can optionally include receiving any number of inputs from a remote monitoring entity (e.g., from a user device of the remote monitoring entity, from a client application of the remote monitoring entity, from a remote computing system in communication with the user device and/or client application of the remote monitoring entity, etc.), such as, but not limited to, any or all of: a set of requests from the remote monitoring entity (e.g., for how the user should be monitored and/or notified), information about the user, information about a program associated with the user, and/or any other information.

This information can then optionally be used for instance, for any or all of: determining a schedule which prescribes when (e.g., how frequently) the user should provide samples at the supplementary alcohol sensing device, determining a level of risk (e.g., criminal vs. non-criminal, repeat offender vs. first offender, etc.) associated with the user, how frequently transdermal samples should be collected, prescribing which actions should be triggered and/or when, and/or can be used in any other way(s).

Additionally or alternatively, the set of inputs can include any other information.

In a first variation, the set of inputs includes sensor information collected at an alcohol sensor along with sensor information collected at a set of supplementary sensors onboard the transdermal alcohol sensing device. Additionally, the set of inputs can include: user information, remote monitoring information, and/or any other information.

In a set of specific examples, the set of supplementary sensors includes a motion sensor (e.g., accelerometer) and a temperature sensor, which collect motion information and temperature information (e.g., body temperature, approximate body temperature, etc.), respectively. Additionally or alternatively, the set of supplementary sensors can include a location sensor (e.g., GPS sensor), a clock, a humidity sensor, a contact sensor, and/or any other sensors.

In a second variation, additional or alternative to the first, the set of inputs includes a set of inputs from a user device associated with the user. These can include sensor information from a set of sensors (e.g., location sensor, motion sensor, temperature sensor, camera, etc.) onboard the user device; information determined at a set of processors onboard the user device; information from memory and/or storage of the user device (e.g., historical measurements); information from the client application and/or a $3^{rd}$ party client application; and/or any other information.

In a set of specific examples, location data associated with the user is collected from the user device, which can be used to determine whether or not a user is within an approved zone (e.g., has not passed a geofence associated with his or her probation). Additionally or alternatively, location data can be collected from the transdermal device (e.g., and compared with location data from the transdermal device to see if the user has potentially left behind his or her transdermal device and/or placed the transdermal device on another user).

In a set of specific examples, a Bluetooth strength between the transdermal device and the user device can be determined at the user device and used to assess the proximity between the devices (e.g., to see if the user has potentially left behind his or her transdermal device and/or placed the transdermal device on another user).

In a third variation, additional or alternative to those above, the set of inputs includes information from a set of sensors associated with a tamper component of the transdermal device, which can be used to detect if a user has tampered with and/or removed the transdermal device. In specific examples, these can include contact sensors associated with a fastener of the transdermal device (e.g., to detect if the user has unfastened the device, to see at what size setting the device is at and if it has changed which might indicate that the device has been placed on a different user, etc.), strain sensors associated with a fastener of the transdermal device (e.g., to detect if the user has unfastened the device, to see at what size setting the device is at and if it has changed which might indicate that the device has been placed on a different user, etc.), and/or any other sensors. Additionally or alternatively, the inputs can include information collected at any or all of the tamper sensors as described in U.S. application Ser. No. 17/033,501, filed 25 Sep. 2020, which is incorporated herein in its entirety by this reference.

4.2 Method—Determining a Set of Outputs S220

The method 200 includes determining a set of outputs S220, which functions to determine an intoxication metric of the user as well as prompt any or all of the actions in S230. In some variations, for instance, the set of outputs further functions to detect if and/or when a user has tampered with and/or detected to tamper with the transdermal device (and/or the supplementary device and/or the user device). Additionally or alternatively, S220 can perform any other suitable functions.

S220 is preferably performed in response to S210, but can additionally or alternatively be performed in absence of S210, in response to another process of the method 200, and/or at any other times and/or in response to any suitable triggers.

The set of outputs is preferably determined at a processing system (e.g., as described above), which can be located at any or all of: the transdermal device, the user device, a supplementary alcohol sensing device, a remote computing system, any other device, and/or at any combination of devices or locations. Additionally or alternatively, the set of outputs can be determined at any other subsystems.

The set of outputs is preferably transmitted to a remote computing system (e.g., from the user device, from the client application, directly from the transdermal device, directly from the supplementary alcohol sensing device, etc.), which can then be accessed by and/or transmitted to devices and/or client applications associated with the remote monitoring entity. Additionally or alternatively, the set of outputs can be transmitted to any other locations, users, and/or devices.

S220 preferably includes generating an intoxication metric based on the set of inputs S222, which functions to assess an intoxication level of the user. The intoxication metric can be any or all of: a TAC value based on an alcohol sensor of the transdermal alcohol sensing device, a BAC value based on an alcohol sensor of a breathalyzer device, a BAC value derived from the TAC value (e.g., with an algorithm and/or model), and/or any other derived intoxication metrics (e.g., qualitative assessment of intoxication). Additionally or alternatively, generating the intoxication metric can include and/or interface with any or all of the methods, processes, embodiments, and/or examples as described in U.S. application Ser. No. 16/362,444, filed 22 Mar. 2019, and U.S. application Ser. No. 17/033,501, filed 25 Sep. 2020, each of which is incorporated herein in its entirety by this reference.

In some variations, for instance, a classification subsystem processes data from the alcohol sensor (e.g., onboard the transdermal alcohol sensing device, onboard the breathalyzer device, etc.) to determine a classification of the user's intoxication and the probability that the user has participated in a drinking event (e.g., consumption of alcohol). The classification subsystem is preferably a machine learning model (e.g., deep learning model, neural network, set of neural networks, etc.), but can additionally or alternatively include programmed and/or rule-based algorithms.

The classification can include: one or more quantitative values (e.g., a particular BAC value, a particular TAC value, a range of TAC and/or BAC values, etc.); one or more qualitative determinations (e.g., a binary determination of sober vs. intoxicated, a type and/or progression of intoxication [e.g., 'sober', 'started drinking,' has been drinking for a while,' 'is intoxicated,' etc.], etc.); and/or any combination.

The classification subsystem can be evaluated at a predetermined frequency (e.g., every 30 minutes using data collected in the last 30 minutes, every hour, between every 5 minutes and every 45 minutes, between every 15 minutes and every 45 minutes, every 2 hours, less than every 2 hours but greater than once per day, etc.), in response to a trigger (e.g., request from a remote monitoring entity, based on a location trigger, based on a motion trigger, based on a temperature trigger, based on an alcohol sample exceeding a predetermined threshold, etc.), randomly (e.g., to perform random checks), and/or at any other times.

In a set of specific examples, a machine learning model processes data collected in S210 (e.g., at a predetermined set of intervals, every 30 minutes, etc.) to determine a probability value (e.g., on a scale from 0 to 1) that the user has participated in a drinking event.

In an additional or alternative set of specific examples, a machine learning model processes data collected in S210 (e.g., at a predetermined set of intervals, every 30 minutes, etc.) to determine a qualitative assessment of the probability (e.g., "low probability" vs. "moderate probability" vs. "high probability") that the user has participated in a drinking event. The qualitative assessment can be determined based on a probability value (e.g., as described above), determined independently of a probability value, and/or otherwise determined.

Additionally or alternatively, a classification subsystem can be used to determine and/or predict any other parameters associated with an intoxication of the user, such as, but not limited to, any or all of: a TAC value associated with the user, a BAC value associated with the user (e.g., determined based on the TAC value and a trained algorithm, determined based on the TAC value and a rule-based algorithm, etc.), a number of drinks consumed by the user, a volume of drinks consumed by the user, a type of drink consumed by the user (e.g., beer vs. wine vs. liquor, an alcohol percentage of the drinks, etc.), a time at which the user began drinking, a time at which the user stopped drinking, and/or any other parameters.

In additional or alternative variations, the intoxication metric can be determined based on any or all of the processes described in U.S. application Ser. No. 16/362,444, filed 22 Mar. 2019, and U.S. application Ser. No. 17/033, 501, filed 25 Sep. 2020, each of which is incorporated herein in its entirety by this reference.

S220 can include generating a set of supplementary parameters based on the set of inputs S224, such as any or all of: motion information associated with the user, temperature information associated with the user, location information associated with the user, and/or any other information. The supplementary parameters can be used for any or all of: determining and/or adjusting (e.g., normalizing) any or all of the alcohol metrics, triggering an action in S230, preventing the triggering of an action in S230, detecting if a user has removed the transdermal alcohol sensing device (e.g., based on zero motion information, based on a temperature measurement being closer to room temperature than body temperature, based on detecting that a baseline signal from the alcohol sensor has collapsed to zero and/or has been otherwise altered relative to historical data, etc.), detecting that a user has tampered with the alcohol sensing device (e.g., placed a piece of fabric and/or paper and/or other barrier over an inlet of the alcohol sensor to prevent their perspiration from being received at the alcohol sensor, placed the device on a different user, etc.), and/or can be used in any other suitable ways.

S220 can optionally additionally include determining collection information associated with receipt of the set of inputs, which functions to detect at which frequency the set of inputs are being received (e.g., synced) at the client application and/or at a remote computing system. This can be used to trigger one or more actions in S230, prevent the triggering of one or more actions in S230, and/or perform any other functions.

S220 can optionally include aggregating any or all of the set of outputs; comparing any or all of the set of outputs with a set of satisfaction criteria (e.g., predetermined thresholds), which can function to determine if an action should be triggered in S230; and/or any other processes. The satisfaction criteria can be any or all of: predetermined, dynamically determined (e.g., based on other sensor information, based on historical information associated with the user, based on patterns associated with the user, etc.), and/or any combination.

In some variations, for instance, S220 includes comparing an intoxication metric with a set of one or more predetermined thresholds (e.g., specific to the user, shared among users, etc.) to determine if a user has been drinking and/or to what extent the user has been drinking.

In additional or alternative variations, S220 can include comparing any or all of the sensor information with a set of thresholds (e.g., to determine if a user has tampered with the device, to adjust the intoxication metric, to adjust the action and/or when it is triggered, etc.). This can include, for instance, any or all of: comparing temperature information with a set of criteria (e.g., thresholds, historical trends of the user, etc.) (e.g., wherein if the temperature falls below an average body temperature threshold, a potential tamper is detected); comparing motion information with a set of criteria (e.g., thresholds, historical trends of the user, etc.) (e.g., wherein if the motion of the user falls below a threshold, a potential tamper is detected due to the device being taken off the user; wherein if the motion is below a predetermined threshold and/or above zero, [and/or that it is nighttime and/or when the user's schedule indicates sleeping] it can be determined that the user is sleeping and that an action does not need to be triggered [yet]; etc.), a potential tamper and/or other features of the user can be detected; comparing alcohol information with a set of criteria (e.g., thresholds, historical trends of the user, etc.) (e.g., wherein if the baseline signal falls below a threshold, a potential tamper is detected due to the device being taken off the user); and/or any other information can be compared with any suitable criteria. Any or all of this sensor information can optionally be: aggregated (e.g., in a weighted fashion, averaged, according to an algorithm, etc.) to determine an aggregated metric (e.g., overall likelihood of tampering) and/or a normalization factor for the intoxication metric.

In a first variation, S220 includes determining a set of intoxication metrics (e.g., continuously, at a sampling frequency, etc.) associated with the user. In a set of specific examples, the set of intoxication metrics includes TAC values. Additionally or alternatively, the set of intoxication metrics includes BAC values. Further additionally or alternatively, the set of intoxication metrics includes qualitative classifications associated with the user's intoxication (e.g., as determined based on TAC values and/or BAC values and/or with an algorithm/model). Additionally or alternatively, the set of intoxication metrics can include any other metrics.

Figure 10:
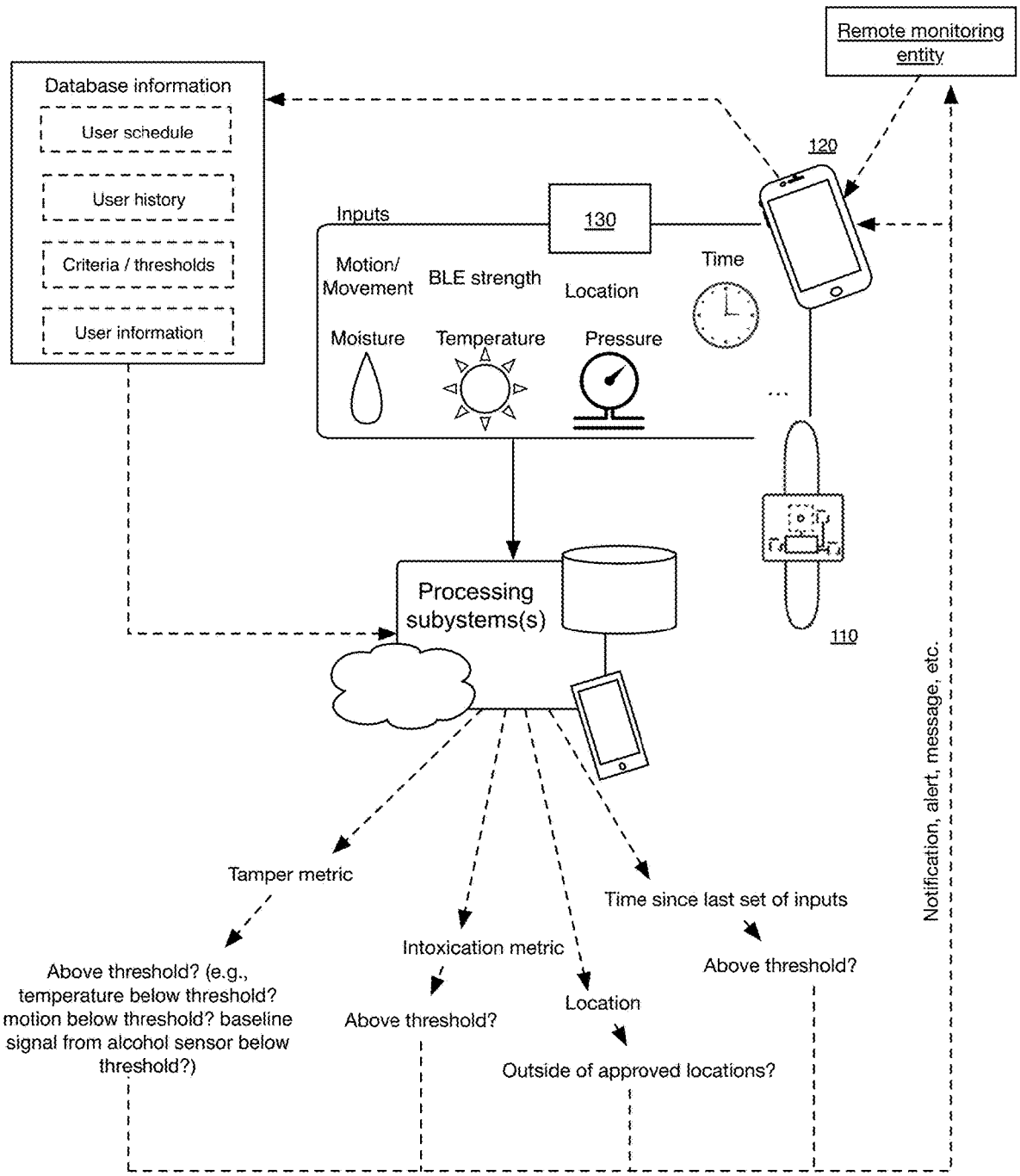
FIG. 10 depicts a schematic variation of a method for remote transdermal alcohol monitoring.

In a second variation (e.g., as shown in FIG. 10), additional or alternative to the first, S220 includes determining a set of tamper metrics (e.g., continuously, at a sampling frequency, etc.) associated with the user. This can be determined based on supplementary sensor information, alcohol information, and/or any other information.

In a third variation, additional or alternative to those described above, S220 includes determining a location associated with the user and comparing it with a set of approved locations associated with the user to see if a user has breached a geofence.

Additionally or alternatively, S220 can include any other processes.

4.3 Method—Triggering an Action Based on the Set of Outputs S230

The method can optionally include triggering an action based on the set of outputs S230, which functions to monitor an intoxication level of the monitored user and to trigger one or more actions in response to any or all of: that intoxication level exceeding a threshold, the device potentially being tampered with (e.g., tamper metric exceeding a threshold), data not being reliably and/or timely received (e.g., exceeding a threshold time period since last data received at remote computing system, exceeding a threshold time period since last data received at user device, etc.) for remote monitoring purposes, the user being located in a forbidden location, and/or any other actions.

In a first variation, S230 includes triggering a notification (e.g., push notification, message, alert, etc.) to be sent to the monitored user (e.g., at the client application, at the transdermal device, at the supplementary device, etc.).

In a first example this variation, a notification (e.g., push notification, message, alert, etc.) is triggered in response to the monitored user having an intoxication level above a predetermined threshold, where the push notification prompts the user to take a second alcohol sample with a breathalyzer device. Additionally or alternatively, a notification can be sent to a remote monitoring entity to alert him or her of the user's intoxication.

In a second example of this variation, a notification (e.g., push notification, message, alert, etc.) is triggered in response to detecting that the user has potentially removed the device and/or tampered with the device, wherein the notification prompts the user to perform a video check in to show that he or she is wearing the device and that it has not been tampered with. Additionally or alternatively, the push notification can prompt the user to take a second alcohol sample with the breathalyzer device. Further additionally or alternatively, a notification can be sent to a remote monitoring entity to alert him or her of the user's tampering.

In a third example of this variation, a notification (e.g., push notification, message, alert, etc.) is triggered in response to detecting that the time elapsed since the last set of inputs was received has exceeded a predetermined threshold (e.g., 1.5 hours, 1 hour, 2 hours, 30 minutes, 15 minutes, between 15 and 45 minutes, between 45 minutes and 1 hour, between 1 hour and 2 hours, greater than 2 hours, etc.). This notification can prompt the user to foreground the client application such that the data is synced from the transdermal alcohol sensing device to the client application and/or from the client application to the cloud (e.g., for viewing by a remote monitoring entity).

In a fourth example, instead of triggering a notification (e.g., push notification, message, alert, etc.) to be sent to the user in response to detecting that the time elapsed since the last set of inputs was received has exceeded a predetermined threshold, the method can instead extend the predetermined threshold to a second longer predetermined threshold based on supplementary information and/or prior alcohol information associated with user. In a specific example, for instance, the method detects that a first threshold of time has been exceeded since data was last received, but also detects that the user is likely sleeping (e.g., based on the time of day, based on the user's schedule and/or normal patterns, based on the user being located in his home, based on the last motion data indicating that his movements are minimal and/or his orientation corresponds to him lying down, based on detecting that the user device is in an overnight charge mode, based on the user's body temperature changing, based on a predictive model, etc.). The method can then do any or all of: reset the threshold time period, wait until a predetermined waking time and/or a waking time of the user to send a push notification if data has still not yet been received, adjust the threshold time period, and/or trigger any other actions.

In a second variation, S230 includes triggering an adjustment of the sampling frequency and/or granularity of collection of location information (and/or any other inputs). In some examples, for instance, the choice between collecting coarse GPS data (e.g., only from cell towers) and fine GPS data (e.g., user's exact location) can be made by the system and/or triggered during the method. In specific examples, for instance, an adjustment from coarse to fine GPS data collection can be made in response to detecting that the user is leaving his or her residence (e.g., based on coarse GPS data, based on motion information from the user, based on an input from the user, based on a schedule of the user, etc.), thereby enabling an accurate determination of the user's whereabouts outside the home to be collected for remote monitoring purposes (e.g., to see if a user has breached a geofence set by his or her probation officer and/or a judge, to see if a user has visited a bar or other place which serves alcohol, to see if the user visits the location of a $2^{nd}$ user with a restraining order against him or her, etc.). In another example, an adjustment can be made from fine to coarse GPS data collection, such as upon detecting that the user is sleeping (e.g., has not changed locations within the last hour and has low motion according to a motion sensor), upon detecting that the fine GPS data collection is lowering the frequency of background syncing for receiving data from the alcohol sensor, and/or based on any other information and/or events.

In a third variation, S230 includes triggering an action based on the user's location. In an example, a detected spike in alcohol can be dismissed based on one or more features of the spike (e.g., duration of drinking event) and/or upon detecting that the spike occurred while the user was at a particular facility (e.g., a hospital where the spike in alcohol corresponds to the user receiving hand sanitizer for a wrist-borne embodiment of the transdermal alcohol sensing device).

Figure 5:
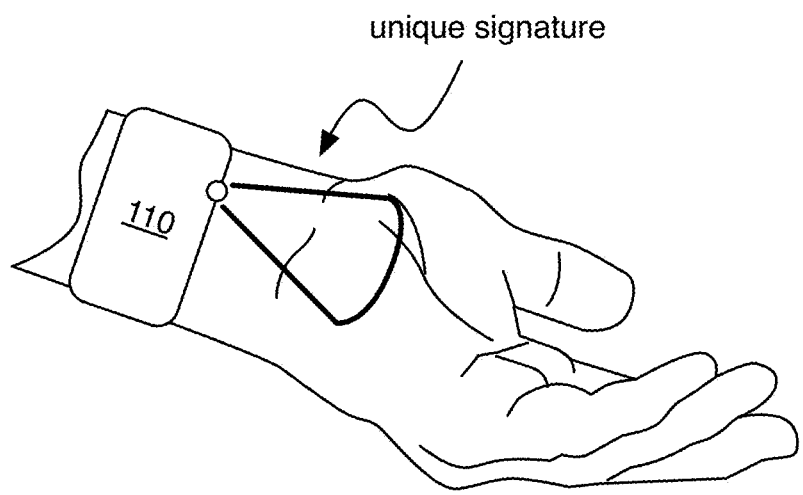
FIG. 5 depicts the emitting of a unique signature at the transdermal alcohol sensing device for verification and/or authentication of the user and his or her alcohol sample.

In a fourth variation, S230 includes prompting the provision of a unique signature (e.g., light signature, acoustic signature, infrared signature, etc.) at one or both of the transdermal alcohol sensing device and the supplementary alcohol sensing device for verification and/or authentication of the monitored user taking an alcohol sample, which can include and/or interface with any or all of the processes as described in U.S. application Ser. No. 14/602,919, filed 22 Jan. 2015, which is incorporated herein in its entirety by this reference. A specific example of the provision of a unique signature is shown in FIG. 5.

Figure 6:
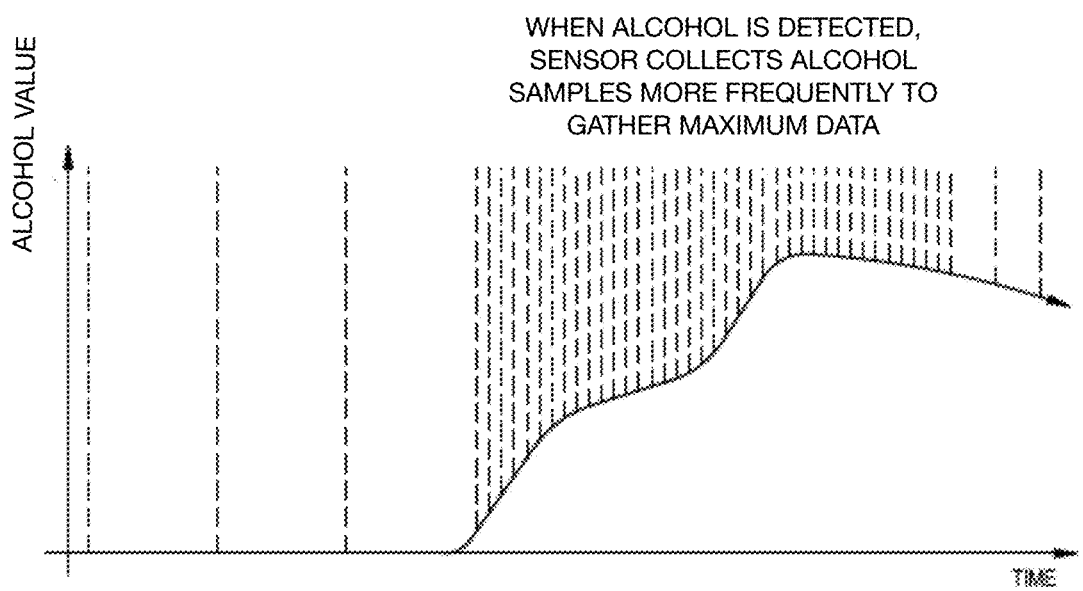
FIG. 6 depicts a variation of triggering the action of adjusting the sampling rate of the transdermal alcohol sensing device in response to detecting intoxication.

In a fifth variation (e.g., as shown in FIG. 6), S230 includes adjusting a sampling rate associated with collection of samples from an alcohol sensor and/or from any other sensors.

Additionally or alternatively, S230 can include triggering any other actions based on any suitable data.

The method 200 can optionally include any other processes performed in any suitable order.

Although omitted for conciseness, the preferred embodiments include every combination and permutation of the various system components and the various method processes, wherein the method processes can be performed in any suitable order, sequentially or concurrently.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

As a person skilled in the art will recognize from the previous detailed description and from the figures and claims, modifications and changes can be made to the preferred embodiments of the invention without departing from the scope of this invention defined in the following claims.

I claim:

1. A method for remote intoxication monitoring of a user with a wearable transdermal alcohol sensing device, the method comprising:
   sampling, at a predetermined frequency:
      a set of parameters from a set of sensors onboard the wearable transdermal alcohol sensing device, the set of parameters comprising:
         an intoxication parameter from a first sensor of the set of sensors;
         a motion parameter from a second sensor of the set of sensors;
         a temperature parameter from a third sensor of the set of sensors;
   transmitting the set of parameters to a client application executing on a user device associated with the user, the user device separate and distinct from the wearable transdermal alcohol sensing device;
   receiving, at a remote computing system, at an intermittent set of intervals associated with a background syncing protocol of the user device:
      the set of parameters from the client application;
   in an event that the set of parameters is not received within a threshold period of time relative to a prior set of parameters:
      triggering a notification at the user device, wherein the notification prompts the user to open the client application, wherein opening the client application automatically triggers a foregrounding of the client application; and
      automatically receiving the set of parameters in response to the user opening the client application;
   determining, based on the set of parameters, an intoxication metric associated with the user; and
   in an event that the intoxication metric exceeds a predetermined threshold, triggering an action.

2. The method of claim 1, wherein the wearable transdermal alcohol sensing device is configured to be worn at a wrist of the user.

3. The method of claim 2, wherein the wearable transdermal alcohol sensing device is configured to be worn at an inner wrist region of the user, the inner wrist region proximal to a palm of a hand of the user.

4. The method of claim 1, wherein the intoxication metric is determined with a trained machine learning model.

5. The method of claim 1, further comprising determining, based on the set of parameters, a tamper parameter associated with the transdermal alcohol sensing device, and in an event that the tamper parameter exceeds a predetermined threshold, triggering a second action.

6. The method of claim 5, wherein the tamper parameter is determined based on at least one of the temperature and motion parameters.

7. The method of claim 6, wherein the tamper parameter is further determined based on the intoxication parameter, wherein the intoxication parameter comprises at least one of a transdermal alcohol concentration (TAC) value and a blood alcohol concentration (BAC) value.

8. The method of claim 7, wherein the tamper parameter is determined at least in part based on the intoxication parameter falling below a predetermined threshold.

9. The method of claim 5, wherein the second action comprises prompting the user to initiate a breathalyzer test with a breathalyzer alcohol sensing device.

10. The method of claim 9, wherein the first action is the same as the second action.

11. The method of claim 9, wherein the breathalyzer alcohol sensing device is separate and distinct from the transdermal alcohol sensing device.

12. The method of claim 5, wherein the second action comprises prompting the user to initiate a video call with remote monitoring entity.

13. The method of claim 1, wherein the intermittent set of intervals has an average frequency value less than the predetermined frequency.

14. The method of claim 1, further comprising receiving at least one of:
a temporal parameter and a user schedule.

15. The method of claim 14, further comprising adjusting the predetermined threshold based on at least one of the temporal parameter and the user schedule.

16. The method of claim 15, further comprising increasing the predetermined threshold in response to determining that the user is suspected to be sleeping based on the at least one of the temporal parameter and the user schedule.

17. The method of claim 16, wherein determining that the user is suspected to be sleeping is further determined based on at least one of the motion parameter and the temperature parameter.

18. A system for remote intoxication monitoring of a user, the system comprising:
a wearable transdermal alcohol sensing device configured to be worn at a wrist of the user, wherein the wearable transdermal alcohol sensing device comprises:
a transdermal alcohol sensor configured to a sample a first parameter at a predetermined frequency;
a motion sensor configured to sample a second parameter at the predetermined frequency; and
a temperature sensor configured to sample a third parameter at the predetermined frequency;
a client application, wherein the client application is executable on a user device associated with the user, the user device separate and distinct from the wearable transdermal alcohol sensing device, wherein the client application is configured to receive the first, second, and third parameters;
a processing subsystem in communication with the transdermal alcohol sensing device and the client application, wherein the processing subsystem is configured to:
receive, at an intermittent set of intervals associated with a background syncing protocol of the user device:
the first, second, and third parameters from the client application;
in an event that the first, second, and third parameters are not received within a threshold period of time relative to a prior set of parameters received from the transdermal alcohol sensor, the motion sensor, and the temperature sensor:
trigger a notification at the user device, wherein the notification promotes the user to open the client application, wherein opening the client application automatically triggers a foregrounding of the client application; and
automatically receive the first, second, and third parameters in response to the user opening the client application;
determine, based on the first, second, and third parameters, an intoxication metric associated with the user; and
in an event that the intoxication metric exceeds a predetermined threshold, trigger an action.

19. The system of claim 18, wherein the transdermal alcohol sensor is a fuel cell sensor.

20. The system of claim 18, wherein the wearable transdermal alcohol sensing device is configured to be worn at an inner wrist region of the user, the inner wrist region proximal to a palm of a hand of the user.

* * * * *

UNITED STATES PATENT AND TRADEMARK OFFICE
CERTIFICATE OF CORRECTION

Page 1 of 1

PATENT NO. : 11,602,306 B2
APPLICATION NO. : 17/574278
DATED : March 14, 2023
INVENTOR(S) : Keith Nothacker It is certified that error appears in the above-identified patent and that said Letters Patent is hereby corrected as shown below:

In the Claims

Column 23, Line 18, In Claim 10, after "wherein the", delete "first"

Column 23, Line 30, In Claim 14, after "of:", delete "¶"

Signed and Sealed this
Twenty-fifth Day of July, 2023

Katherine Kelly Vidal
*Director of the United States Patent and Trademark Office*